(12) United States Patent  
Tanaka et al.

(10) Patent No.: US 9,370,303 B2  
(45) Date of Patent: Jun. 21, 2016

(54) OPHTHALMOLOGIC APPARATUS AND METHOD FOR CONTROLLING THE SAME

(71) Applicant: CANON KABUSHIKI KAISHA, Tokyo (JP)

(72) Inventors: Hiroyoshi Tanaka, Tokyo (JP); Futoshi Hirose, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 281 days.

(21) Appl. No.: 14/063,975

(22) Filed: Oct. 25, 2013

(65) Prior Publication Data

US 2014/0118697 A1  May 1, 2014

(30) Foreign Application Priority Data

Oct. 26, 2012 (JP) .................. 2012-236797  
Oct. 26, 2012 (JP) .................. 2012-236798  
Oct. 26, 2012 (JP) .................. 2012-236799  
Sep. 2, 2013 (JP) .................. 2013-181188

(51) Int. Cl.
*A61B 3/14* (2006.01)
*A61B 3/02* (2006.01)

(52) U.S. Cl.
CPC ...................... *A61B 3/14* (2013.01)

(58) Field of Classification Search
USPC ......... 351/200, 204–206, 208, 211, 212, 221, 351/222, 225, 243–245
See application file for complete search history.

(56) References Cited

U.S. PATENT DOCUMENTS

2014/0146286 A1* 5/2014 Suzuki ................... A61B 3/117  
351/206  
2014/0232846 A1* 8/2014 Tanaka ................. G02B 21/365  
348/79

OTHER PUBLICATIONS

Zhang et al."High-speed volumetric imaging of cone photoreceptors with adaptive optics spectraldomain optical coherence tomography" Optics Express, May 2006, pp. 4380-4394, vol. 14, No. 10.

* cited by examiner

*Primary Examiner* — Joseph P Martinez  
*Assistant Examiner* — Brandi Thomas  
(74) *Attorney, Agent, or Firm* — Canon USA Inc., IP Division

(57) ABSTRACT

An adaptive optics (AO) optical system is used, to perform accurate alignment between the AO optical system and a subject's eye. An ophthalmologic apparatus according to the present invention includes a positional relationship change unit (e.g., a driving mechanism including a stage for moving the apparatus) configured to change a positional relationship between a subject's eye and an optical system including an aberration measurement unit (e.g., a Shack-Hartmann wavefront sensor) in a first irradiation state of the subject's eye with measurement light, and an irradiation state change unit (e.g., a mechanism for changing an irradiation position) configured to change an irradiation state of the subject's eye with the measurement light from the first irradiation state to a second irradiation state for correcting an aberration of the subject's eye based on a measurement result of the aberration measurement unit.

16 Claims, 20 Drawing Sheets

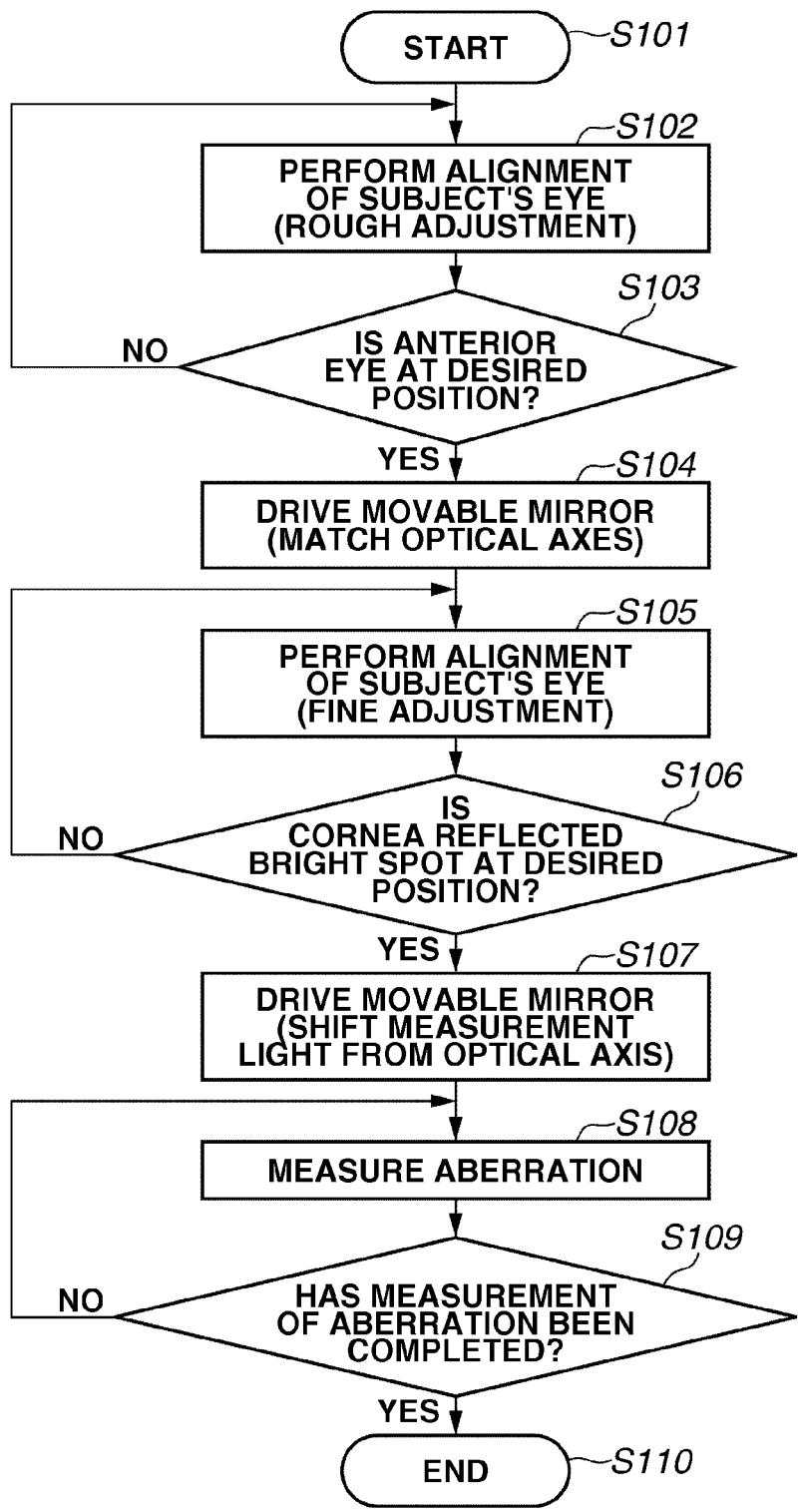

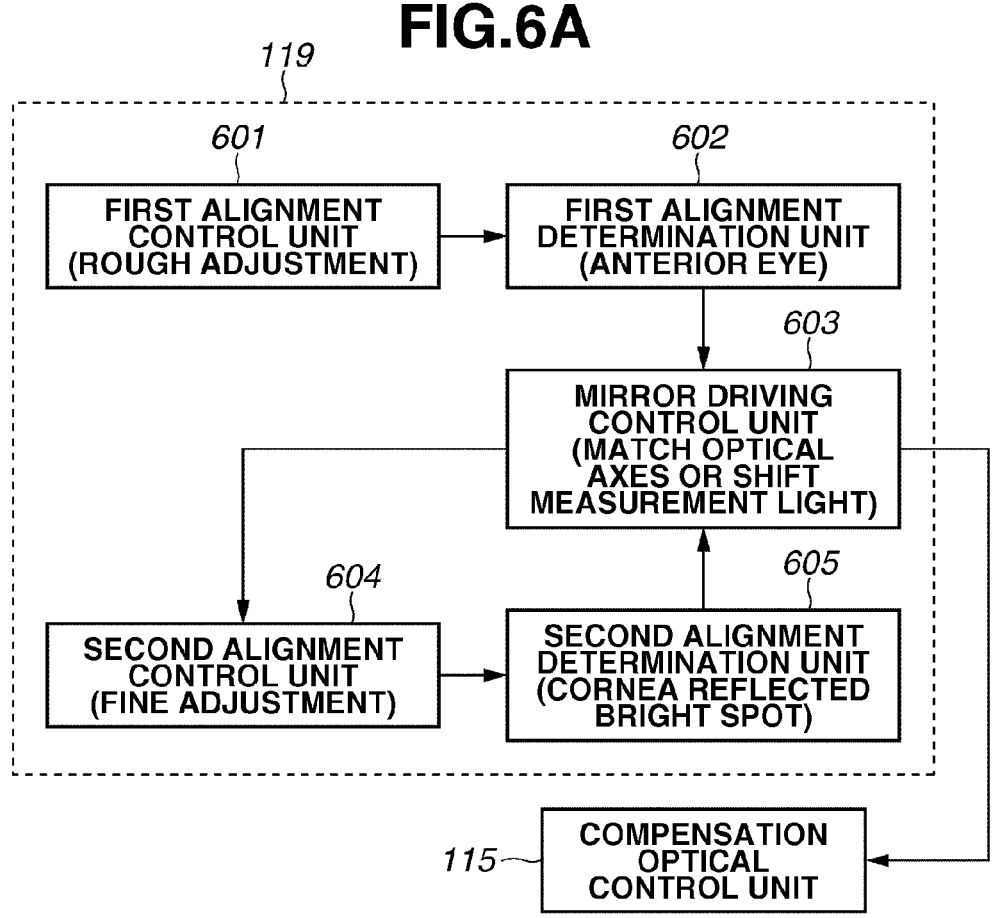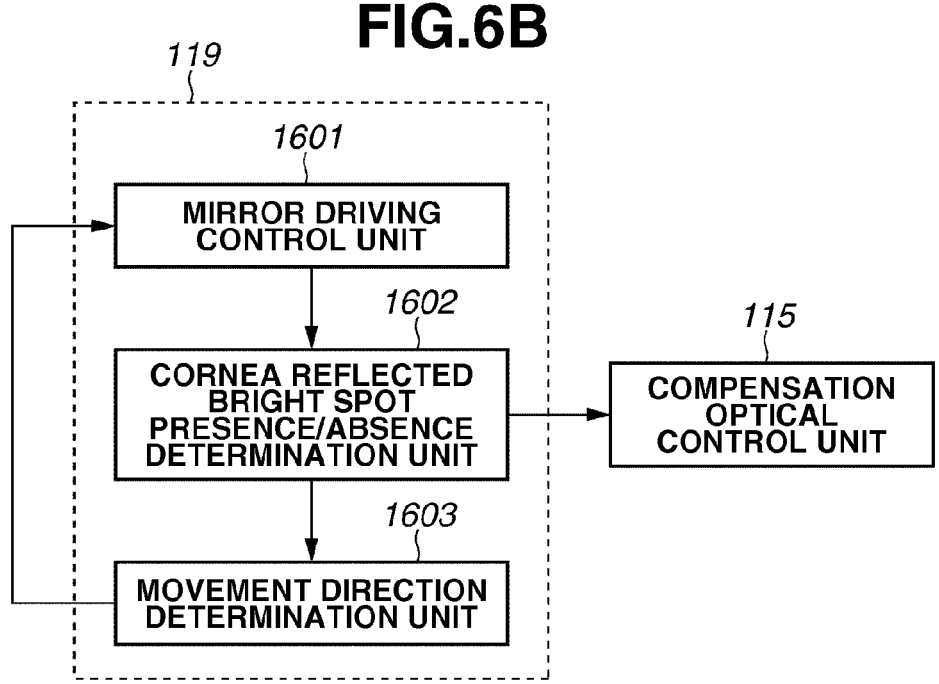

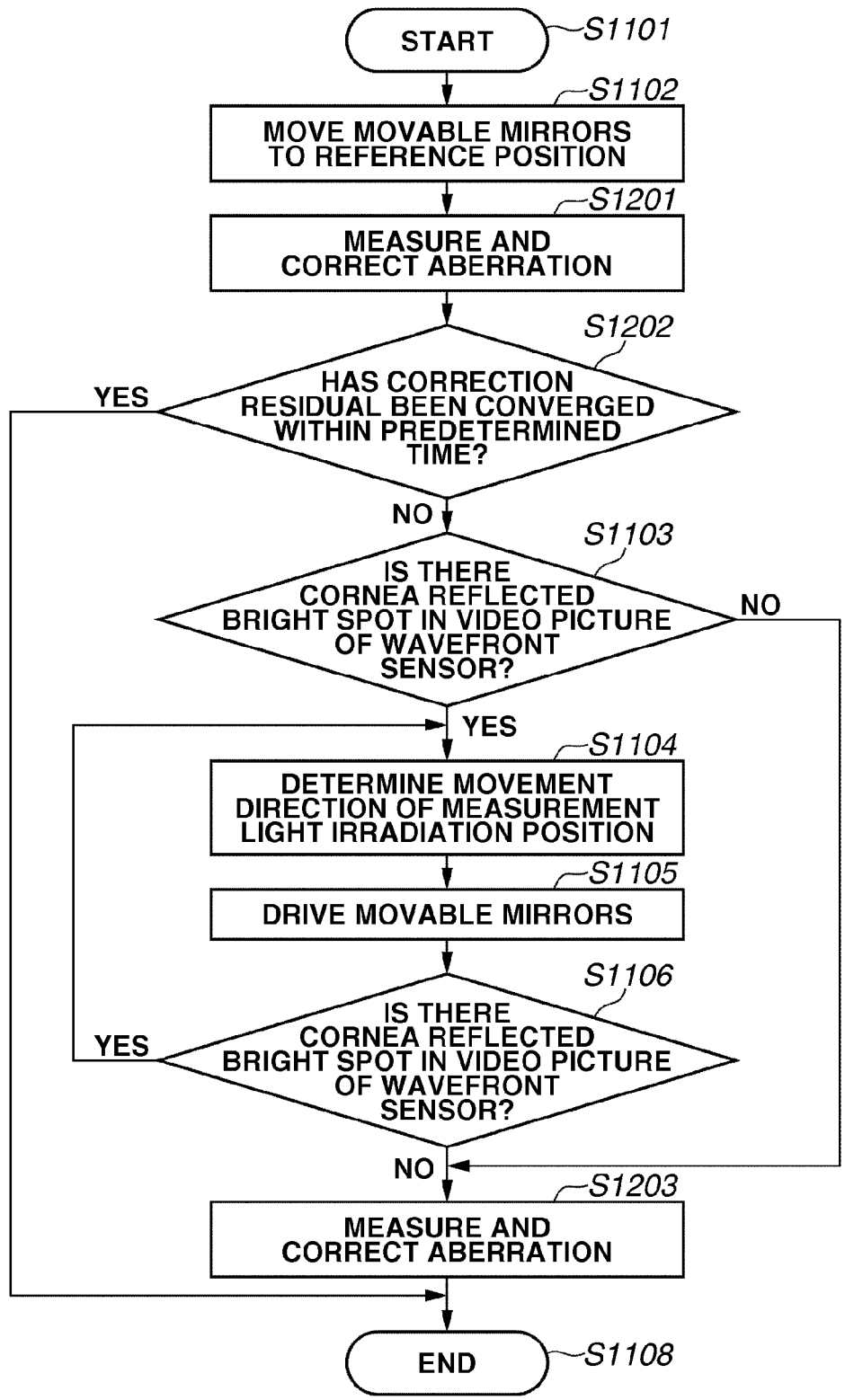

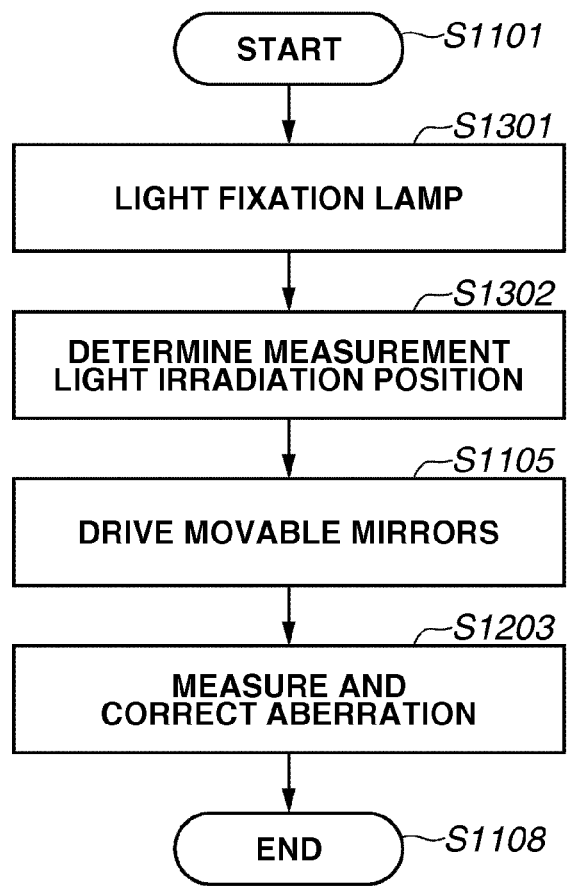

OPHTHALMOLOGIC APPARATUS AND METHOD FOR CONTROLLING THE SAME

BACKGROUND OF THE INVENTION

1. Field of the Invention

The present invention relates to an ophthalmologic apparatus configured to measure an aberration of a subject's eye, and a method for controlling the same.

2. Description of the Related Art

In recent years, an ophthalmologic apparatus has included a scanning laser ophthalmoscope (SLO) apparatus, which scans laser light two-dimensionally on a fundus of a subject's eye, receives light reflected from the fundus, and acquires a two-dimensional image of the fundus, and an optical coherence tomography (OCT) apparatus, which acquires a tomographic image of the fundus using interference of low coherent light. The type of the OCT mainly includes a time domain OCT (TD-OCT) and a fourier domain OCT (FD-OCT). The type of the FD-OCT includes a spectral domain OCT (SD-OCT) and a swept source OCT (SS-OCT).

In recent years, the resolution of such an ophthalmologic apparatus has been increased by increasing the numerical aperture (NA) of a laser irradiation optical system. At this time, if a fundus of a subject's eye is imaged, measurement light needs to pass through an optical structure, such as a cornea or a crystalline lens, of the subject's eye. Thus, the captured image quality of a fundus image may be deteriorated due to an influence exerted by an aberration of the cornea or the crystalline lens. Therefore, an AO-SLO and an AO-OCT, which incorporate adaptive optics (AO) for measuring the aberration of the subject's eye and correcting the aberration into an optical system, are discussed in Y. Zhang et al, Optics Express, Vol. 14, No. 10, 15 May 2006. If the aberration of the subject's eye is measured, a Shack-Hartmann wavefront sensor system is generally used. This system first condenses a laser on a retina of the subject's eye, irradiates the condensed laser, and then receives light, which has passed through a pupil of the subject's eye, in reflected and scattered light from the retina using a sensor such as a charge coupled device (CCD) camera via a microlens array so that a wavefront can be measured based on a light receiving result. A wavefront correction device such as a variable shape mirror or a spatial phase modulator is driven so that the measured wavefront is corrected. Thus, a fundus having a high resolution can be imaged.

SUMMARY OF THE INVENTION

The present invention is directed to an ophthalmologic apparatus and method for controlling the same capable of accurately correcting an aberration by performing accurate alignment between an AO optical system and a subject's eye.

According to an aspect of the present invention, an ophthalmologic apparatus includes an aberration measurement unit configured to measure an aberration of a subject's eye, a positional relationship change unit configured to change a positional relationship between the subject's eye and an optical system including the aberration measurement unit in a first irradiation state of an anterior eye of the subject's eye with measurement light, and an irradiation state change unit configured to change an irradiation state of the anterior eye of the subject's eye with the measurement light from the first irradiation state to a second irradiation state for correcting the aberration of the subject's eye based on a measurement result of the aberration measurement unit.

According to another aspect of the present invention, a method for controlling an ophthalmologic apparatus, includes changing a positional relationship between a subject's eye and an optical system including an aberration measurement unit in a first irradiation state of an anterior eye of the subject's eye with measurement light, changing an irradiation state of the anterior eye of the subject's eye with the measurement light from the first irradiation state to a second irradiation state, and correcting an aberration of the subject's eye based on a measurement result of an aberration of the subject's eye in the second irradiation state.

Further features of the present invention will become apparent from the following description of exemplary embodiments with reference to the attached drawings.

BRIEF DESCRIPTION OF THE DRAWINGS

FIG. 5 is a flowchart illustrating a method for controlling the aberration measurement apparatus according to the first exemplary embodiment.

FIGS. 6A and 6B are block diagrams respectively illustrating methods for controlling aberration measurement apparatuses according to the first exemplary embodiment and a fourth exemplary embodiment.

FIG. 13 is a flowchart illustrating a method for controlling the aberration measurement apparatus according to the fifth exemplary embodiment.

FIG. 15 is a flowchart illustrating a method for controlling the aberration measurement apparatus according to the sixth exemplary embodiment.

DESCRIPTION OF THE EMBODIMENTS (Change in Irradiation State of Subject's Eye with Measurement Light)

A first exemplary embodiment will be described. However, the present invention is not limited to this.

If a subject's eye is measured or if a fundus image of the subject's eye is acquired, the subject's eye and an ophthalmologic apparatus need to be aligned with each other. Generally, a method for performing the alignment while irradiating an anterior eye of the subject's eye with alignment light from an optical system (camera) for alignment and confirming a cornea reflected bright spot image with an anterior eye camera, is considered.

Even if the optical system for alignment is accurately aligned with the subject's eye, an AO optical system (an optical system including a Shack-Hartmann wavefront sensor) serving as an optical system different from the optical system for alignment is not necessarily accurately aligned with the subject's eye due to an influence exerted by a tolerance generated when the ophthalmologic apparatus has been assembled. When the alignment is thus performed using the optical system for alignment different from the AO optical system, an aberration is not easy to accurately correct depending on precision of the alignment between the AO optical system and the subject's eye.

Figure 3A:
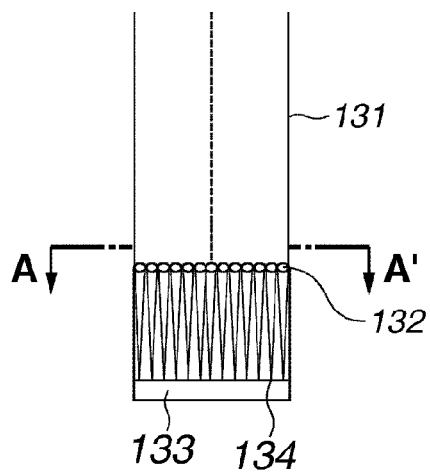
FIGS. 3A to 3F are schematic diagrams illustrating a wavefront sensor according to the first exemplary embodiment.
Figure 3B:
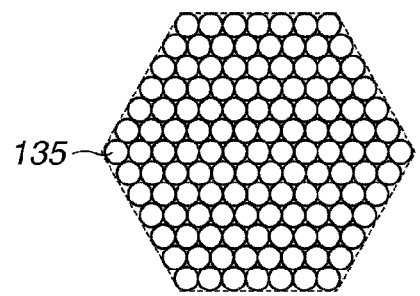
Figure 3C:
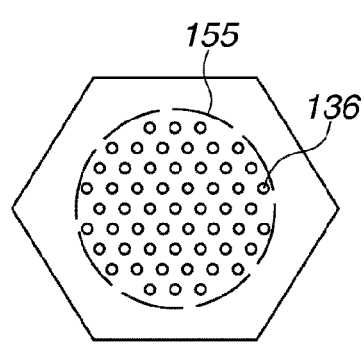
Figure 3D:
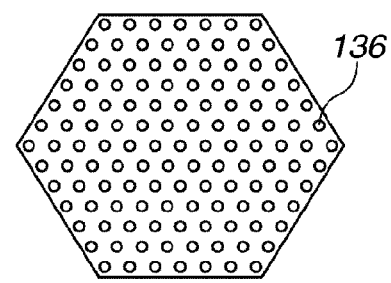

If the Shack-Hartmann wavefront sensor receives light, a circular light portion corresponding to a pupil of the subject's eye (see FIG. 3C representing the Shack-Hartmann wavefront sensor) is acquired. The above-mentioned alignment can be accurately performed so that the circular light portion moves to a substantial center of the wavefront sensor. If the pupil of the subject's eye is large or if the pupil is mydriatic, however, the entire wavefront sensor becomes a light portion (see FIG. 3D representing the Shack-Hartmann wavefront sensor). Thus, the alignment is not easy to perform using the light portion.

One purpose of the present exemplary embodiment is to perform accurate alignment between an AO optical system and a subject's eye, to accurately correct an aberration of the subject's eye in view of the above-mentioned problem.

An ophthalmologic apparatus (also referred to as an aberration measurement apparatus that measures an aberration of a subject's eye) according to the present exemplary embodiment first includes a positional relationship change unit (e.g., a driving mechanism including a stage for moving the ophthalmologic apparatus), which changes a positional relationship between the subject's eye and an optical system (AO optical system) including an aberration measurement unit (e.g., a Shack-Hartmann wavefront sensor) in a first irradiation state of the subject's eye with measurement light. The aberration measurement apparatus according to the present exemplary embodiment includes an irradiation state change unit (described below), which changes an irradiation state of the subject's eye with the measurement light from the first irradiation state to a second irradiation state for correcting the aberration of the subject's eye based on a measurement result of the aberration measurement unit.

If a pupil of the subject's eye is large or if the pupil is mydriatic, therefore, a cornea reflected bright spot image, which has been acquired by the aberration measurement unit, can be displayed on a display unit such as a monitor, for example. Thus, the AO optical system and the subject's eye can be accurately aligned with each other. After the alignment has been completed, an irradiation state (e.g., an irradiation position, an irradiation shape, and an irradiation area) of the subject's eye can be changed. Therefore, the aberration can be accurately corrected (Change in Irradiation State).

The irradiation state change unit may preferably change the irradiation position of the subject's eye with the measurement light. Thus, the aberration measurement unit does not acquire the cornea reflected bright spot image when the aberration is measured. Therefore, the aberration can be accurately measured. For example, an optical axis of an optical system of measurement light 104 may preferably be moved toward an optical axis of an SLO optical system with respect to an optical path splitting unit (e.g., a beam splitter 107) provided in the SLO optical system. More specifically, the irradiation state change unit may preferably include a movement unit, which moves a position of a movable mirror 105 provided in the optical system of the measurement light 104 serving as a splitting optical path in an optical axis direction from the optical path splitting unit. The movable mirror 105 is movable in the optical axis direction, and includes a movable stage and a beam steering, for example. In this case, the first irradiation state is a state where a position including a substantial center of the subject's eye is irradiated with the measurement light 104, and a second irradiation state is a state where a position not including the substantial center of the subject's eye is irradiated with the measurement light 104. The present invention is not limited to the foregoing as long as an optical axis of an optical system including a light source 101, which generates the measurement light 104, may preferably be moved from an optical axis of the subject's eye. Thus, the alignment and the aberration correction can be performed without moving an optical axis of an optical system including an aberration correction unit. The change in the irradiation position will be described in detail in the first exemplary embodiment.

The irradiation state change unit may preferably change an irradiation shape and an irradiation area of the measurement light 104 in the subject's eye. Thus, the aberration measurement unit can perform accurate alignment and aberration measurement without shifting the optical axis of the optical system of the measurement light 104. At this time, the irradiation shape may preferably be changed with the optical axis of the light source 101, which generates the measurement light 104, and the optical axis of the subject's eye substantially matched. The irradiation area may preferably be changed with the optical axis of the light source 101, which generates the measurement light 104, and the optical axis of the subject's eye not matched. The changes in the irradiation shape and the irradiation area will be described in detail in second and third exemplary embodiments.

The aberration measurement apparatus according to the present exemplary embodiment may preferably include a determination unit configured to determine whether the change in the positional relationship has been completed. At this time, the irradiation state change unit can automatically measure the aberration by changing the irradiation state of the measurement light 104 from the first irradiation state to the second irradiation state according to a determination result of the determination unit.

(Change in Irradiation Position of Subject's Eye with Measurement Light)

The second exemplary embodiment will be described below. However, the present invention is not limited to this.

Light, which has been mirror surface-reflected on a surface of a cornea of a subject's eye, is higher in intensity than reflected and scattered light from a retina of the subject's eye, which is required to measure a wavefront. When the light, which has been mirror surface-reflected on the surface of the cornea, enters a wavefront sensor, the reflected and scattered light from the retina is buried in the light, which has been mirror surface-reflected on the surface of the cornea. As a result, an aberration of the subject's eye cannot be measured with high-accuracy. Generally, the aberration of the subject's eye is measured at a position where an incidence position of measurement light is shifted from an eye axis of the subject's eye so that the measurement light is reflected in a direction different from a direction toward the wavefront sensor on the surface of the cornea.

A line of sight (a visual axis) of the subject's eye may be changed using a fixation target. If the line of sight of the subject's eye is changed while an irradiation position with the measurement light is changed from an optical axis, a reflection position on the surface of the cornea is also changed as the cornea rotates and moves. As a result, mirror surface reflected light from the cornea may enter the wavefront sensor. In this case, complicated work is required. For example, a user changes relative positions of the subject's eye and an optical system. Thus, a period of time elapsed until the aberration is measured so that a burden on a subject is increased. If the subject's eye has a small pupil diameter, the measurement light may be vignetted (shielded) by an iris of the subject's eye by merely changing the irradiation position with the measurement light. Therefore, a period of time elapsed until the aberration is measured is increased, and accordingly the burden on the subject is increased.

One purpose of the present exemplary embodiment is to shorten a period of time required to measure the aberration, to reduce the burden on the subject. Thus, in the present exemplary embodiment, a good irradiation position with the measurement light, which is not affected by a cornea reflected bright spot or the vignetting (shielding) by the iris, is efficiently irradiated with the measurement light.

An ophthalmologic apparatus (also referred to as an aberration measurement apparatus that measures an aberration of a subject's eye) according to the present exemplary embodiment includes a determination unit configured to determine the presence or absence of a cornea reflected bright spot image corresponding to reflected light on a cornea of the subject's eye based on a measurement result of an aberration measurement unit, which measures the aberration of the subject's eye. The ophthalmologic apparatus according to the present exemplary embodiment further includes an irradiation position change unit configured to change an irradiation position of the subject's eye with measurement light based on the measurement result of the aberration measurement unit when it is determined that the cornea reflected bright spot image exists. With this configuration, a good irradiation position, which is not affected by a cornea reflected bright spot or vignetting (shielding) by an iris of the subject's eye, can be efficiently irradiated with the measurement light. Therefore, a period of time required to measure the aberration can be shortened, and therefore, a burden on a subject can be reduced.

The irradiation position change unit may preferably move an optical axis of an optical system of measurement light 104 toward an optical axis of an SLO optical system with respect to an optical splitting unit (e.g., a beam splitter 107) provided in the SLO optical system, for example. More specifically, the irradiation position change unit may preferably include a movement unit, which moves respective positions of movable mirrors 105-1 and 105-2 provided in the optical system of the measurement light 104, serving as a splitting optical path, in an optical axis direction from the optical path splitting unit (a driving mechanism 106 that drives the movable mirrors 105-1 and 105-2). The movable mirrors 105-1 and 105-2 are movable in the optical axis direction, and each include a movable stage and a beam steering, for example. The present invention is not limited to the foregoing as long as an optical axis of an optical system including a light source 101, which generates the measurement light 104, can be moved from an optical axis of the subject's eye. Thus, the alignment and aberration correction can be performed without moving an optical axis of an optical system including an aberration correction unit. The change in the irradiation position will be described in detail in a fourth exemplary embodiment.

The ophthalmologic apparatus according to the present exemplary embodiment may preferably include a determination unit configured to determine a direction in which the irradiation position is changed based on the measurement result of the aberration measurement unit, and change the irradiation position in the determined direction. The ophthalmologic apparatus may preferably include a display control unit configured to display on a display unit the cornea reflected bright spot image measured by the aberration measurement unit and the determined direction. With this configuration, a user can easily visually recognize that a good irradiation position, which is not affected by the cornea reflected bright spot or the vignetting (shielding) by the iris, is irradiated with the measurement light 104.

The ophthalmologic apparatus according to the present exemplary embodiment may preferably include a fixation target position change unit configured to change a position of a fixation target. The determination unit may preferably determine the presence or absence of the cornea reflected bright spot image after the fixation target position change unit has changed the position of the fixation target. Through this operation, even if the cornea reflected bright spot enters a wavefront sensor because a line of sight of the subject's eye has been changed, the irradiation position can be changed so that the cornea reflected bright spot does not enter the wavefront sensor. As a result, the accuracy of the aberration measurement can be improved.

The ophthalmologic apparatus according to the present exemplary embodiment may preferably include a positional relationship change unit configured to change a positional relationship between the subject's eye and an optical system (AO optical system) including an aberration measurement unit (e.g., a Shack-Hartmann wavefront sensor) (e.g., a driving mechanism including a stage that moves the ophthalmologic apparatus). At this time, the determination unit may preferably determine the presence or absence of the cornea reflected bright spot image after the positional relationship change unit has changed the positional relationship to a predetermined positional relationship (alignment has been performed). Through this operation, even if the cornea reflected bright spot enters the wavefront sensor because the subject's eye moves after the alignment has been performed, the irradiation position can be changed so that the cornea reflected bright spot does not enter the wavefront sensor. Thus, the accuracy of the aberration measurement can be improved.

(Presentation of Irradiation Position of Subject's Eye with Measurement Light to Operator)

The third exemplary embodiment will be described below. However, the present invention is not limited to this. One purpose of the present exemplary embodiment is to shorten a period of time required to measure an aberration, to reduce burden on a subject, like in the second exemplary embodiment. Thus, in the present exemplary embodiment, an operator is notified that an irradiation position with measurement light should be changed to a good irradiation position that is not affected by a cornea reflected bright spot or vignetting (shielding) by an iris of a subject's eye.

An ophthalmologic apparatus (also referred to as an aberration measurement apparatus that measures an aberration of a subject's eye) according to the present exemplary embodiment includes a determination unit configured to determine the presence or absence of a cornea reflected bright spot image corresponding to reflected light on a cornea of the subject's eye based on a measurement result of an aberration measurement unit configured to measure the aberration of the subject's eye. The ophthalmologic apparatus according to the present exemplary embodiment includes a display control unit configured to display on a display unit a display format representing the cornea reflected bright spot image when it is determined that the cornea reflected bright spot image exists. With this configuration, the operator can be notified that an irradiation position with the measurement light should be changed to a good irradiation position that is not affected by a cornea reflected bright spot or vignetting (shielding) by an iris of the subject's eye. Therefore, a period of time required to measure the aberration can be shortened, and therefore, a burden on a subject can be reduced. The cornea reflected bright spot image corresponds to the irradiation position of the subject's eye with the measurement light.

In the display format representing the cornea reflected bright spot image, an area having intensity, which is a threshold value or more, in an image obtained by receiving light by a wavefront sensor can be colored with red, or can be indicated by an arrow. The display format representing the cornea reflected bright spot image may be displayed in any notification method as long as a user understands that the cornea reflected bright spot image is included in the wavefront sensor.

The ophthalmologic apparatus according to the present exemplary embodiment includes a determination unit configured to determine a direction in which the irradiation position of the subject's eye with the measurement light is changed based on the measurement result of the aberration measurement unit. A display control unit may preferably display on a display unit a display format representing the cornea reflected bright spot image and a display format representing the determined direction. If an amount in which the irradiation position is to be changed is also displayed in addition to the direction, user convenience is improved, and the period of time required to measure the aberration can be further shortened, and the burden on the subject can be reduced.

The ophthalmologic apparatus may preferably include a selection unit configured to select either one of an automatic mode for automatically changing the irradiation position and a manual mode for manually changing the irradiation position by a designation unit. If the manual mode is selected, for example, an irradiation position change unit can change the irradiation position to a position that has been designated by the designation unit such as a joystick or a mouse.

The irradiation position change unit may preferably move an optical axis of an optical system of measurement light 104 toward an optical axis of an SLO optical system with respect to an optical path splitting unit (e.g., a beam splitter 107) provided in the SLO optical system, for example. More specifically, the irradiation position change unit may preferably include a movement unit configured to move a position of a movable mirror 105 provided in the optical system of the measurement light 104, serving as a splitting optical path, in an optical axis direction from the optical path splitting unit (a driving mechanism 106 that drives the movable mirror 105). The movable mirror 105 is movable in the optical axis direction, and includes a movable stage and a beam steering, for example. The present invention is not limited to the foregoing as long as an optical axis of an optical system including a light source 101 configured to generate the measurement light 104 can be moved from an optical axis of the subject's eye. Thus, the alignment and aberration correction can be performed without moving an optical axis of an optical system including an aberration correction unit. The change in the irradiation position will be described in detail in a seventh exemplary embodiment.

The ophthalmologic apparatus according to the present exemplary embodiment includes a fixation target position change unit configured to change a position of a fixation target. The determination unit may preferably determine the presence or absence of a cornea reflected bright spot image after the fixation target position change unit has changed the position of the fixation target. Through this operation, Even if the cornea reflected bright spot enters the wavefront sensor because a line of sight of the subject's eye has been changed, therefore, the irradiation position can be changed so that the cornea reflected bright spot does not enter the wavefront sensor. Therefore, the accuracy of the aberration measurement can be improved.

The ophthalmologic apparatus according to the present exemplary embodiment may preferably include a positional relationship change unit configured to change a positional relationship between the subject's eye and an optical system (AO optical system) including an aberration measurement unit (e.g., a Shack-Hartmann wavefront sensor) (e.g., a driving mechanism including a stage for moving the ophthalmologic apparatus). At this time, the determination unit may preferably determine the presence or absence of the cornea reflected bright spot image after the positional relationship change unit has changed the positional relationship to a predetermined positional relationship. Through this operation, even if the cornea reflected bright spot enters the wavefront sensor because the subject's eye moves after being aligned, the irradiation position can be changed so that the cornea reflected bright spot does not enter the wavefront sensor. Therefore, the accuracy of the aberration measurement can be improved.

(Change in Positional Relationship Between Subject's Eye and AO Optical System Based on Aberration Measurement Result)

The fourth exemplary embodiment will be described below. The positional relationship change unit may preferably change the positional relationship based on a measurement result of an aberration measurement unit. For example, the positional relationship can be changed so that a circular light portion 155 illustrated in FIG. 3C corresponding to a pupil of a subject's eye, which has been measured by the aberration measurement unit, is positioned in a predetermined range (or at a substantial center) of the aberration measurement unit. If the pupil of the subject's eye is large or if the pupil is mydriatic, the positional relationship can also be changed so that a cornea reflected bright spot image, which has been acquired by the aberration measurement unit, is positioned in a predetermined range of the aberration measurement unit. In this way, accurate alignment between an AO optical system and the subject's eye can be automatically performed.

The positional relationship change unit may preferably include a display control unit (not illustrated) configured to display on a display unit the cornea reflected bright spot image that has been acquired by the aberration measurement unit, and an input unit configured to input a signal for an operator to change the positional relationship. With this configuration, the operator can manually perform the accurate alignment between the AO optical system and the subject's eye.

(Focus Adjustment)

A fifth exemplary embodiment will be described below with reference to FIGS. 20A to 20D. FIG. 20A to 20D are diagrams illustrating focus adjustment performed when an irradiation position of a subject's eye with measurement light is shifted from the apex of a cornea of the subject's eye.

Figure 20A:
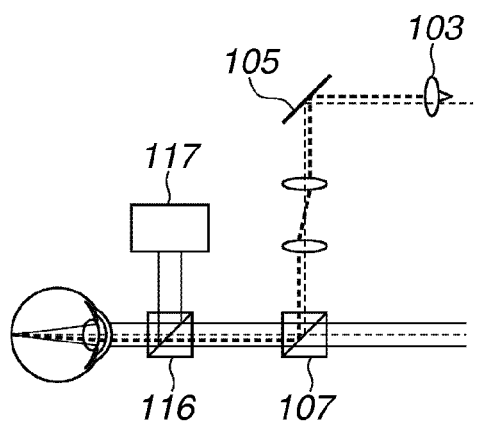
FIGS. 20A to 20D are diagrams illustrating focus adjustment performed when an irradiation position of a subject's eye with measurement light is shifted from the apex of a cornea of the subject's eye.
Figure 20C:
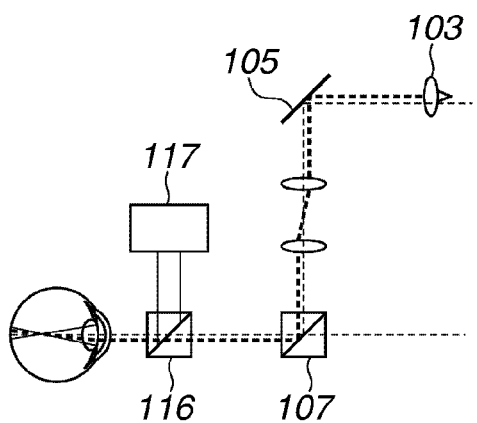
Figure 20B:
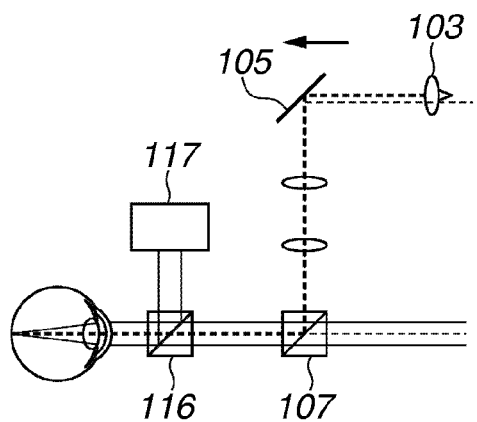
Figure 20D:
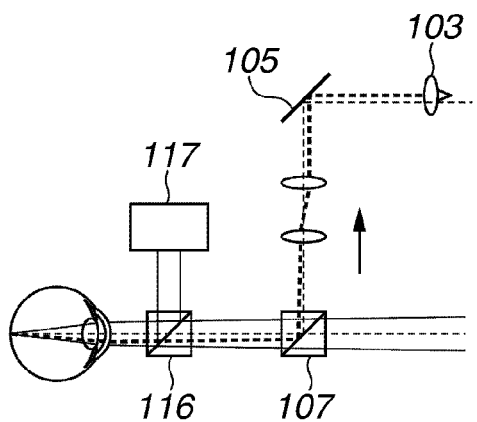

If the diopter D of the subject's eye is substantially zero, the measurement light is first focused on a fundus of the subject's eye even if a position of a movable mirror 105 is moved in an optical axis direction, as illustrated in FIGS. 20A and 20B. A case where the subject's eye is a myopic eye will be described with reference to FIGS. 20C and 20D, which are similar in position of an optical system to FIG. 20A. At this time, the measurement light is focused in front of a retina of the subject's eye. Thus, a focus lens provided between the movable mirror 105 and a beam splitter 107 is moved in the optical axis direction, as illustrated in FIG. 20D. Through this operation, an aberration can be measured with high-accuracy with the measurement light focused on the retina.

The above-mentioned exemplary embodiments will be described in detail below in a first example to an eighth example.

(Change in Irradiation Position)

Figure 1:
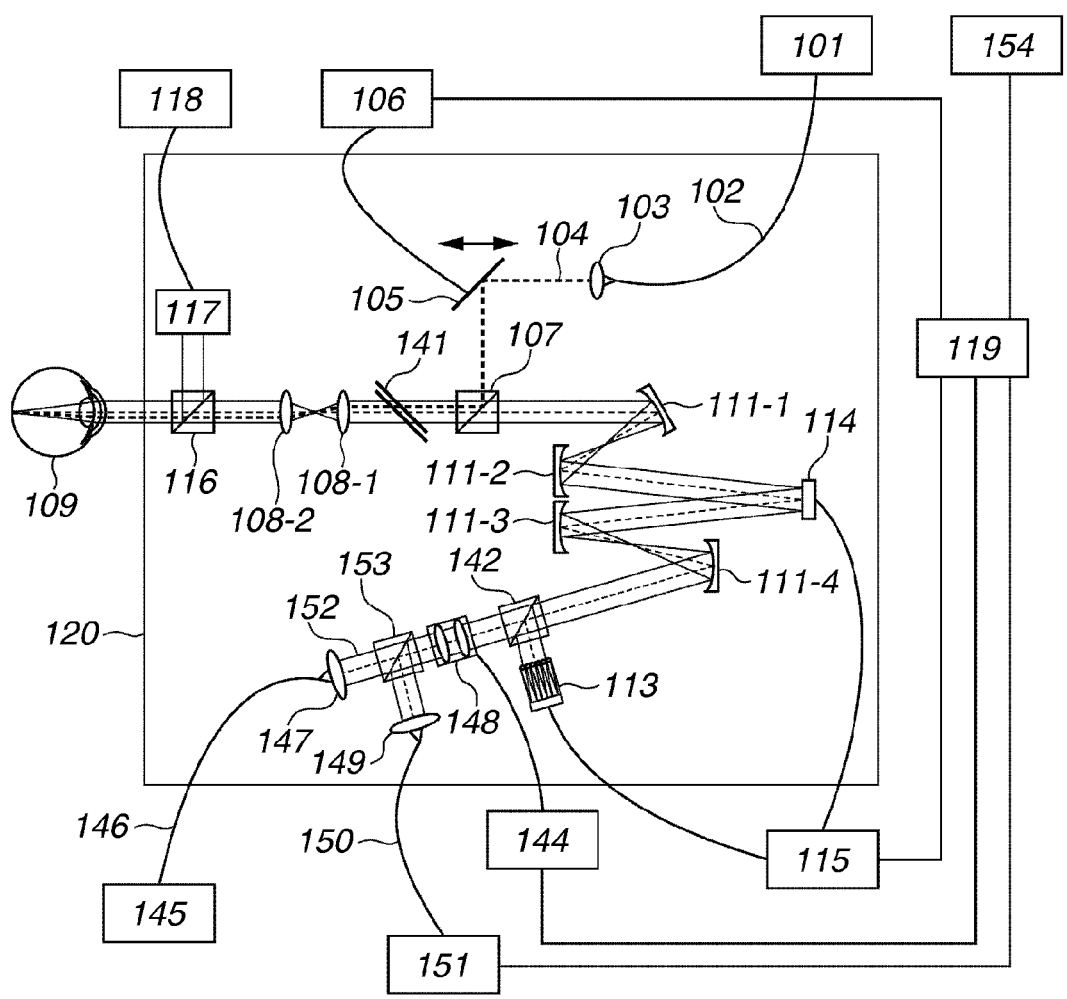
FIG. 1 is a schematic diagram illustrating an aberration measurement apparatus according to a first exemplary embodiment.

FIG. 1 is a schematic diagram illustrating an aberration measurement apparatus according to the first exemplary embodiment. The first exemplary embodiment is an example of an SLO with a compensation optical function. An imaging apparatus according to the present invention is not limited to the SLO according to the present exemplary embodiment, and is also applicable to an OCT.

A compensation optical system will be described below. A light source 101 is a super luminescent diode (SLD) light source having a wavelength of 760 nm. While the wavelength of the light source 101 is not particularly limited, the light source 101 appropriately has a wavelength close to or identical to that of an SLO light source 145, described below, from a viewpoint of a chromatic aberration. Irradiation light of the SLO light source 145 may be branched when used. While the SLO light source 145 is used in the present exemplary embodiment, a laser may be used in addition thereto. Measurement light 104, which has been irradiated from the light source 101, is irradiated as a parallel ray by a collimator 103 via a single mode optical fiber 102. The irradiated measurement light 104 is irradiated onto a subject's eye 109 via a scanning optical system 141, objective lens 108-1 to 108-2, and an eyepiece beam splitter 116 after being reflected on a movable mirror 105 and further reflected on a beam splitter 107. The movable mirror 105 changes an irradiation position of the subject's eye 109 with the measurement light 104. When an alignment mode and an aberration measurement mode are switched, the irradiation position with the measurement light 104 can be changed therewith. This point will be described in detail below.

A driving mechanism 106 for the movable mirror 105 is a linear motion shaft, which is implemented by a motor and a ball screw, for example. The driving mechanism 106 may be implemented by a solenoid or a cylinder in addition thereto. While the scanning optical system 141 uses two galvano scanners for main scanning (in a fundus horizontal direction, i.e., an X-direction) and sub-scanning (a fundus vertical direction, i.e., a Y-direction) in the present exemplary embodiment, a resonance scanner can also be used on the main scanning side of the scanning optical system 141 to perform higher-speed imaging. Depending on a configuration, an optical element such as a mirror or a lens may be used between the scanners within the scanning optical system 141 to make the scanners optically conjugate with one another. In the present exemplary embodiment, the scanning optical system 141 is required when a fundus image is captured. Thus, the scanning optical system 141 remains stationary at a position of a scanning angle of in a process of measuring an aberration. To correct an influence exerted by a tolerance generated when the ophthalmologic apparatus has been assembled, the scanner may be made to stand still at an appropriate offset angle. Such illumination in which the measurement light 104 is condensed on a retina of the subject's eye 109 to match the diopter of the subject's eye 109 becomes possible by adjusting respective positions of the objective lens 108-1 and 108-2. While a lens is used as an eyepiece portion, the eyepiece portion may be composed of a spherical mirror. An anterior eye observation camera 117 observes an anterior eye of the subject's eye 109 via the eyepiece beam splitter 116, and a state of the anterior eye is reflected on a monitor 118. A position of an optical system 120 is roughly adjusted using a driving mechanism (not illustrated) including a stage so that a position of the subject's eye 109 becomes a predetermined position on the monitor 118. Reflected and scattered light, which has been reflected or scattered from the retina, travels to the beam splitter 107 in an opposite direction on an incidence path of the reflected and scattered light, and passes through the beam splitter 107. Then, the reflected and scattered light is sequentially reflected on reflection mirrors 111-1 and 111-2, a wavefront correction device 114, and reflection mirrors 111-3 and 111-4, is reflected on a beam splitter 142, and is guided to a wavefront sensor 113. The reflection mirrors 111-1 to 111-4 are installed so that at least the pupil of the subject's eye 109 and the wavefront sensor 113 or the wavefront correction device 114 are optically conjugate with each other.

(Wavefront Correction Device)

Figure 2A:
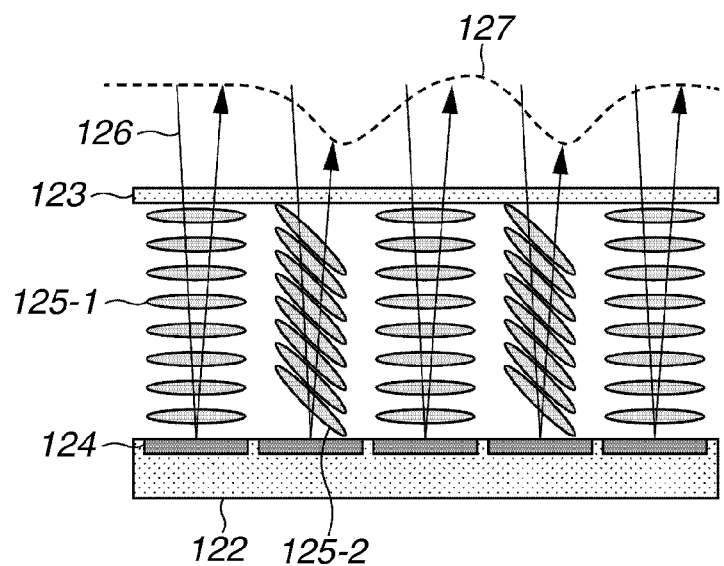
FIGS. 2A and 2B are schematic diagrams illustrating a wavefront correction device according to the first exemplary embodiment.

In the present exemplary embodiment, a spatial phase modulator using a liquid crystal element is used as the wavefront correction device 114 (also referred to as an aberration correction device). FIG. 2A is a schematic diagram of a reflection type liquid crystal optical modulator. In the reflection type liquid crystal optical modulator, liquid crystal molecules 125 are sealed in a space sandwiched between a base portion 122 and a cover 123. The base portion 122 includes a plurality of pixel electrodes 124, and the cover 123 includes a transparent counter electrode (not illustrated). If no voltage is applied between the electrodes, the liquid crystal molecules 125 are in an orientation state 125-1. When a voltage is applied between the electrodes, the liquid crystal molecules 125 are shifted to an orientation state 125-2 so that a refractive index to incident light 126 is changed. When a voltage of each of the pixel electrodes 124 is controlled to change a refractive index of each pixel, spatial phase modulation can be performed. If the incident light 126 is incident on the reflection type liquid crystal optical modulator, for example, the incident light 126, which passes through the liquid crystal molecules 125 in the orientation state 125-2, is delayed in phase than the incident light 126, which passes through the liquid crystal molecules 125 in the orientation state 125-1. As a result, a wavefront 127 is formed. Generally, the reflection type liquid crystal optical modulator includes tens of thousands of pixels to hundreds of thousands of pixels. The liquid crystal element has a polarization property. Thus, a polarizing element for adjusting polarization of the incident light 126 may be provided on an incident optical path of the reflection type liquid crystal optical modulator.

Figure 2B:
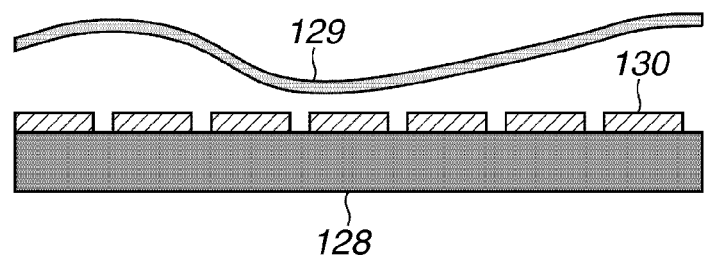

Another example of the wavefront correction device 114 is a variable shape mirror. The variable shape mirror can locally change a light reflection direction. Variable shape mirrors of various types are put into practical use. The variable shape mirrors include one having a cross section, as illustrated in FIG. 2B. The variable shape mirror includes a deformable film mirror surface 129, which reflects the incident light, a base portion 128, an actuator 130 sandwiched between the mirror surface 129 and the base portion 128, and a support portion (not illustrated), which supports the mirror surface 129 from its circumference. An operation principle of the actuator 130 includes ones using an electrostatic force, a magnetic force, and a piezoelectric effect. A configuration of the actuator 130 differs depending on the operation principle. A plurality of actuators 130 is arranged in a two-dimensional manner on the base portion 128. When the actuators 130 are selectively driven, the mirror surface 129 can be freely deformed. Generally, the variable shape mirror includes tens of thousands of actuators to hundreds of thousands of actuators.

(Wavefront Sensor)

The reflected and scattered light, which has been reflected on the reflection mirrors 111-3 and 111-4 and the beam splitter 142, is irradiated onto the wavefront sensor 113, and is used to measure a wavefront of a light ray. In the present exemplary embodiment, a Shack-Hartmann wavefront sensor is used as the wavefront sensor 113. FIGS. 3A and 3B are schematic diagrams of the Shack-Hartmann wavefront sensor. A light ray 131 having a wavefront to be measured is condensed on a focal plane 134 on a CCD sensor 133 via a microlens array 132. FIG. 3B is a diagram illustrating how the Shack-Hartmann wavefront sensor is viewed from a line A-A' illustrated in FIG. 3A. The microlens array 132 includes a plurality of microlenses 135. The light ray 131 is condensed on the CCD sensor 133 after being divided into spots 136, the number of which corresponds to the number of the microlenses 135. A state where the light ray 131 has been condensed on the CCD sensor 133 differs, as illustrated in FIGS. 3C and 3D, depending on which of the thickness of the reflected and scattered light (return light) and the wavefront sensor 113 is larger. The light ray 131, which has passed through each of the microlenses 135, is condensed on the spot 136. If the pupil diameter of a pupil of the subject's eye 109 is small, the thickness of the reflected and scattered light becomes smaller than that of the wavefront sensor 113, as illustrated in FIG. 3C. In this case, an image, which has been received by the CCD sensor 133, becomes a circular light portion 155 corresponding to the pupil. On the other hand, if the pupil diameter of the subject's eye 109 is large (or if the pupil is mydriatic), the thickness of the reflected and scattered light becomes larger than that of the wavefront sensor 113, as illustrated in FIG. 3D. In this case, the reflected and scattered light is received on the entire surface of the CCD sensor 133 so that the image becomes a light portion in a shape corresponding to the entire surface.

Figure 3E:
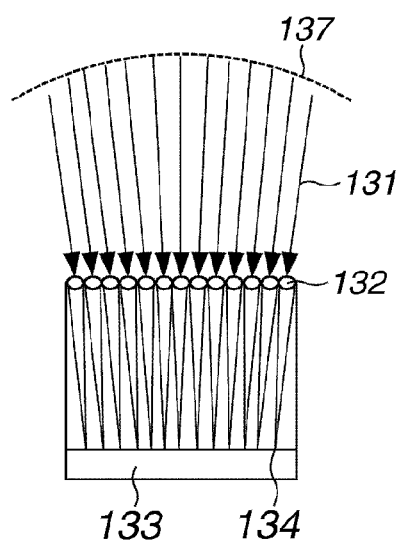
Figure 3F:
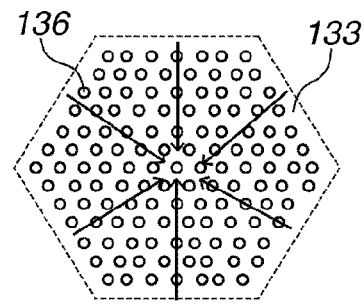

The wavefront of the incident light ray 131 is calculated based on a position of each of the spots 136, which have been condensed by the microlens 135. For example, FIG. 3E is a schematic diagram illustrating a case where a wavefront having a spherical aberration has been measured. The light ray 131 is formed of a wavefront 137. The microlens array 132 condenses the light ray 131 on a local position in a perpendicular direction of the wavefront 137. A condensing state of the CCD sensor 133 in this case is illustrated in FIG. 3F. Since the light ray 131 has a spherical aberration, the spot 136 is condensed in a deviated state toward the center. The wavefront 137 of the light ray 131 can be found by calculating the position. A wavefront sensor, which is applicable to the present invention, is not limited to the Shack-Hartmann wavefront sensor as long as it can measure a wavefront. The wavefront sensor includes a wavefront curvature sensor. The wavefront curvature sensor can measure a wavefront based on a change in a light brightness distribution on the front and back sides of a light traveling direction.

The wavefront sensor 113 is connected to a compensation optical control unit 115, and transmits a wavefront of received light to the compensation optical control unit 115. The wavefront correction device 114 is also connected to the compensation optical control unit 115, and performs modulation designated from the compensation optical control unit 115. The compensation optical control unit 115 calculates such a modulation amount that the wavefront, which has been acquired from the wavefront sensor 113, is corrected to a wavefront having no aberration, and instructs the wavefront correction device 114 to perform the modulation. The measurement of the wavefront and the instruction to the wavefront correction device 114 are repeatedly processed, and feedback control is performed so that the wavefront always becomes optimum.

(Optical System of SLO)

An optical system of the SLO will be described below. An example of the light source 145 is an SLD light source having a wavelength of 840 nm. The wavelength of the light source 145 is not particularly limited. However, a wavelength of approximately 800 to 1500 nm is appropriately used to reduce glare of a subject and maintain resolution as a light source for imaging a fundus. While the SLD light source is used in the present exemplary embodiment, a laser can also be used in addition thereto.

Measurement light 152, which has been irradiated from the light source 145, is irradiated as a parallel ray by a collimator 147 via a single mode optical fiber 146. The irradiated measurement light 152 is incident on a resolution change unit 148 after passing through a light splitting unit 153 including a beam splitter.

The resolution change unit 148 can change the resolution by changing the beam diameter of the incident measurement light 152 and emitting the measurement light 152. Imaging can be performed with a resolution of approximately 3 µm to 20 µm on the fundus by changing the beam diameter in a range of approximately 7 mm to 1 mm. It is useful to make the resolution variable to lower the resolution to suppress a data amount during imaging at a wide angle, to adjust the resolution depending on the aberration of the subject's eye 109, and to perform imaging while avoiding a site having a low transmittance with a narrow beam depending on an imaging method. The resolution change unit 148 is controlled from the resolution control unit 144, and the resolution control unit 144 operates in cooperation with the control unit 119. The resolution change unit 148 may preferably have a configuration in which any one of a plurality of lenses is inserted into an optical path or a configuration in which a diaphragm having a changeable size is provided in an optical path. Thus, the resolution can be continuously changed or discretely changed.

The measurement light 152, which has passed through the resolution change unit 148, is incident on the compensation optical system after passing through the light splitting unit 142. Then, the measurement light 152 is irradiated onto the subject's eye 109 after traveling through the scanning optical system 141 in a direction opposite to that when the aberration is measured and being scanned by the scanning optical system 141. Return light from the subject's eye 109 returns to the light splitting unit 153 along the same optical path, is partially reflected on the light splitting unit 153, and is guided to a light intensity sensor 151 via a collimator 149 and an optical fiber 150. An image acquisition unit (not illustrated) included in the control unit 119 generates a fundus image of the subject's eye 109 (a tomographic image of the subject's eye 109 in the case of an OCT) using an electric signal obtained by converting the light received by the light intensity sensor 15. A display control unit (not illustrated) included in the control unit 119 displays the fundus image on a display 154 serving as an example of the display unit. A display 154 and the monitor 118 may be a common display unit. The display unit may be provided in a main body of the ophthalmologic apparatus, or may be provided as a monitor of a personal computer (PC) separately from the ophthalmologic apparatus.

(Change in Irradiation Position)

A change in an irradiation position of the subject's eye 109 according to the present exemplary embodiment and a change in a positional relationship between the subject's eye 109 and an apparatus (particularly, the optical system 120) will be described with reference to FIGS. 4A to 4D. FIGS. 4A to 4D are schematic diagrams illustrating the change in the irradiation position of the subject's eye 109, which has been irradiated with the measurement light 104, by the aberration measurement apparatus according to the present exemplary embodiment.

Figure 4A:
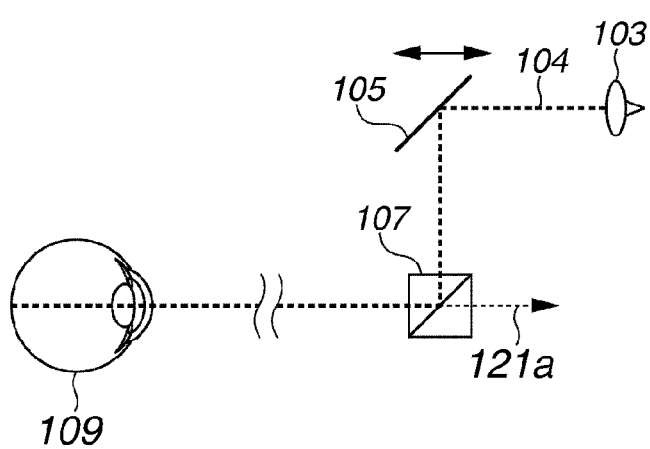
FIGS. 4A to 4D are schematic diagrams illustrating a change in an irradiation position of a subject's eye, which has been irradiated with measurement light, by the aberration measurement apparatus according to the first exemplary embodiment.
Figure 4B:
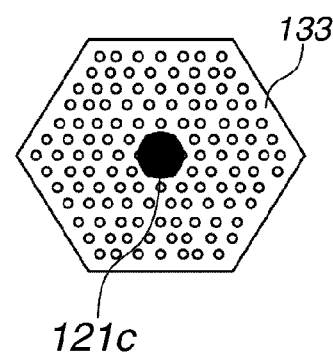

FIG. 4A illustrates a state where a position of the movable mirror 105 is driven so that the measurement light 104 matches an optical axis of the compensation optical system and a case where the apex of the cornea of the subject's eye 109 is on the optical axis of the compensation optical system. At this time, cornea reflected light 121a obtained by mirror surface-reflecting the measurement light 104 on the apex of the cornea of the subject's eye 109 is mixed into the compensation optical system, and is guided to the wavefront sensor 113. As illustrated in FIG. 4B, a bright spot 121c, which is brighter than the others, is reflected in the CCD sensor 133 by receiving the cornea reflected light 121a. If the apex of the cornea of the subject's eye 109 is slightly shifted from the optical axis of the compensation optical system, a position of the bright spot 121c on the CCD sensor 133 is shifted from the center of the CCD sensor 133. At this time, respective positions of the subject's eye 109 and the compensation optical system can be adjusted by operating a driving mechanism for the compensation optical system so that the position of the bright spot 121c is guided to the center of the CCD sensor 133. A video picture of the CCD sensor 133 may be provided with a bright spot alignment target at any position by adding various types of offsets caused by the aberration measurement apparatus and an optical system of the subject's eye 109.

Figure 4C:
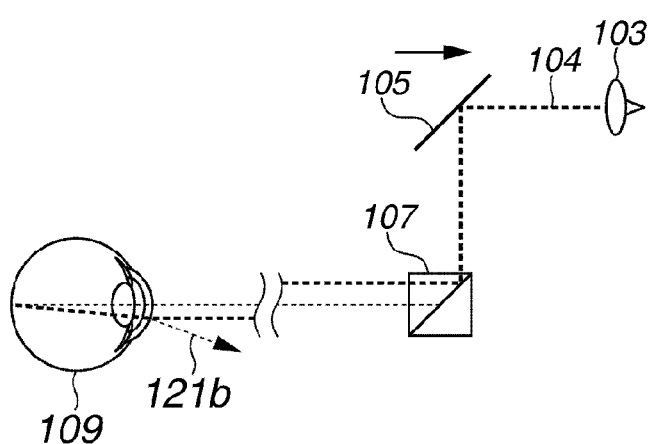
Figure 4D:
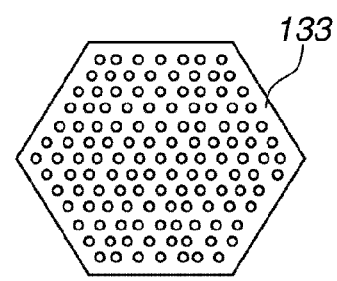

The aberration cannot be measured with the bright spot 121c reflected. When the alignment is completed, the movable mirror 105 is driven, to shift (move) the measurement light 104 from the optical axis of the compensation optical system, as illustrated in FIG. 4C. At this time, the cornea reflected light 121a changes in a direction indicated by an arrow 121b. Thus, the cornea reflected light 121a is not mixed into the compensation optical system, so that the aberration can be measured, as illustrated in FIG. 4D. A position of the bright spot 121C on the retina, on which the measurement light 104 is condensed, is a focal position of the optical system of the subject's eye 109. If the measurement light 104 is shifted in a direction parallel to the optical axis, positions of the bright spot on the retina before and after the shift substantially match each other, and an influence on the aberration measurement can be negligibly small. While a shift amount to the subject's eye 109 in the present exemplary embodiment is approximately 0.5 to 1.0 mm, the present invention is not limited to this.

(Method for Controlling Aberration Measurement Apparatus)

A method for controlling the aberration measurement apparatus according to the present exemplary embodiment will be described below with reference to a flowchart of FIG. 5 and a block diagram of FIG. 6A. In step S101, first, a control start unit (not illustrated) starts to control the aberration measurement apparatus. In step S102, a first alignment control unit 601 then receives a signal from the control start unit, to perform rough alignment (rough adjustment in a positional relationship between the subject's eye 109 and the aberration measurement apparatus). At this time, the above-mentioned rough adjustment is performed by controlling a driving mechanism for the optical system 120 or an operator manually operating the driving mechanism so that an image of an anterior eye of the subject's eye 109 displayed on the monitor 118 is at a desired position. More specifically, a method for performing adjustment so that a pupil of the subject's eye 109 comes to the center of the monitor 118 may be used, or a method for displaying an alignment target for guiding some of features of the anterior eye on the monitor 118 may be used. In step S103, the first alignment determination unit 602 determines whether the anterior eye is at a desired position (the above-mentioned rough adjustment has been completed) upon receiving a signal from the first alignment control unit 601. This determination may be manually performed by the operator, or may be automatically performed by the aberration measurement apparatus using image information processing performed by the control unit 119.

If it is determined that the rough adjustment has been completed (YES in step S103), then in step S104, the mirror driving control unit 603 drives the movable mirror 105 upon receiving a signal from the first alignment determination unit 602, to match an optical axis of the measurement light 104 with an optical axis of the compensation optical system. Timing of driving of the movable mirror 105 in step S104 need not be after the rough adjustment, and may be any timing before proceeding to step S105 (e.g., steps S101 to S103). A designation unit (not illustrated) may preferably designate a change mode for performing alignment (a fine adjustment mode) after the driving. In step S105, the second alignment control unit 604 performs high-accuracy alignment (fine adjustment) by controlling a driving mechanism for the optical system 120 or the operator manually operating the driving mechanism so that a cornea reflected bright spot appearing on an image of the CCD sensor 133 in the wavefront sensor 113 is at a desired position upon receiving a signal from the mirror driving control unit 603.

In step S106, the second alignment determination unit 605 determines whether the cornea reflected bright spot is at the desired position (the above-mentioned fine adjustment has been completed) upon receiving a signal from the second alignment control unit 604. If it is determined that the fine adjustment has been completed (YES in step S106), then in step S107, the mirror driving control unit 603 drives the movable mirror 105, to shift (move) the measurement light 104 from the optical axis of the compensation optical system upon receiving a signal from the second alignment determination unit 605. After the driving, a designation unit (not illustrated) may preferably designate a measurement mode for measuring the aberration of the subject's eye 109 according to a determination result of the determination unit.

In step S108, the compensation optical control unit 115 controls the wavefront sensor 113 upon receiving the signal from the mirror driving control unit 603, and measures the aberration while the cornea reflected light is not measured. In step S109, the compensation optical control unit 115 determines whether the aberration has been measured. If it is determined that the aberration has been measured (YES in step S108), the processing proceeds to step S110. In step S110, control of the aberration measurement apparatus is ended. After the aberration has been corrected based on the measured aberration, an image acquisition unit (not illustrated) then acquires the fundus image of the subject's eye 109 using the light source 145. While each of the units 601 to 605 is included in the control unit 119, the present invention is not limited to this. The unit may be provided separately from the control unit 119.

According to the present exemplary embodiment, alignment of the subject's eye 109 having a wide pupil or being widened with an AO optical system can be performed with high-accuracy. Thus, the aberration can be measured with high-accuracy. To perform high-accuracy alignment using a wavefront sensor for aberration measurement, a movable mirror may be only added to the aberration measurement apparatus so that a configuration of the apparatus can be simplified. Further, adjustment is performed using the cornea reflected bright spot. Thus, the adjustment is easy and is easily understandable for the operator.

(Change in Irradiation Shape)

Figure 7A:
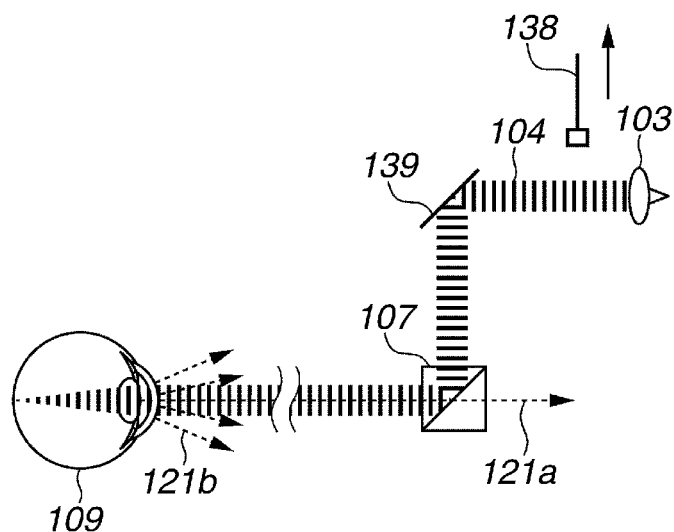
FIGS. 7A and 7B are schematic diagrams illustrating a change in an irradiation shape of a subject's eye, which has been irradiated with measurement light, by an aberration measurement apparatus according to a second exemplary embodiment.
Figure 7B:
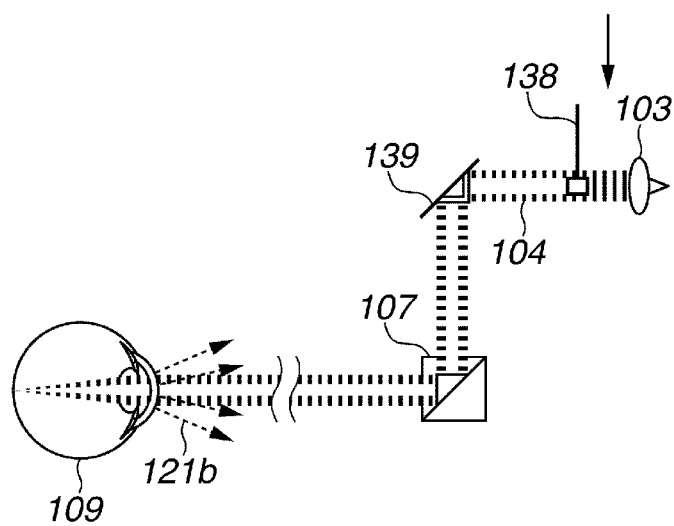

The second exemplary embodiment will be described below with reference to FIGS. 7A and 7B. FIGS. 7A and 7B are schematic diagrams illustrating a change in an irradiation shape of a subject's eye 109, which has been irradiated with measurement light 104 by an aberration measurement apparatus according to the present exemplary embodiment. The present exemplary embodiment is an example in which cornea reflected light is controlled using a ring-shaped illumination shape. A configuration of the aberration measurement apparatus according to the present exemplary embodiment is similar to that in the first exemplary embodiment except for an irradiation portion with the measurement light 104.

As illustrated in FIG. 7A, the measurement light 104, which has been reflected on a fixed mirror 139, is irradiated onto the subject's eye 109 coaxially with an optical axis of a compensation optical system by a beam splitter 107. A circular shielding plate 138 for changing the measurement light 104 into a ring illumination is positioned outside an optical path of the measurement light 104 in a process of alignment between the subject's eye 109 and the compensation optical system. The shielding plate 138 is an example of a beam attenuation unit, which is detachably attached to an optical system of the measurement light 104 and attenuates a part of the measurement light 104. At this time, the measurement light 104 is condensed by an optical system of the subject's eye 109, to form a bright spot on a retina of the subject's eye 109. When the measurement light 104 passes through a cornea of the subject's eye 109, a part of the measurement light 104 is mirror surface-reflected on a surface of the cornea, and reflected light is radially reflected on a convex surface. When the apex of the cornea of the subject's eye 109 exists on the optical axis of the compensation optical system, cornea reflected light 121*a* of the measurement light 104, which has been reflected on the apex of the cornea, is mixed into the compensation optical system, and the bright spot is reflected in the wavefront sensor 113. When the apex of the cornea of the subject's eye 109 is slightly shifted from the optical axis of the compensation optical system, a position of a bright spot 121*c* on a CCD 133 is also shifted. Thus, the subject's eye 109 and the compensation optical system can be aligned with each other.

As illustrated in FIG. 7B, a driving unit then moves the shielding plate 138 to a position where an optical axis portion of the measurement light 104 is shielded to measure an aberration when the alignment has been completed. The driving unit is implemented by a motor, a solenoid, or a cylinder (not illustrated). The diameter of the shielding plate 138 is set smaller than the diameter of the measurement light 104, so that the measurement light 104 has a hollow ring shape. The ring-shaped measurement light 104 is irradiated onto the subject's eye 109 after passing through the fixed mirror 139, the beam splitter 107, and an eyepiece optical system (not illustrated). Consequently, the measurement light 104, which has been irradiated onto the apex of the cornea, is completely shielded by the shielding plate 138. Thus, the cornea reflected light 121*a* fades away so that the bright spot disappears from the wavefront sensor 113. While the measurement light 104, which has been changed into the ring shape after passing through the shielding plate 138, decreases in luminance depending on a shielded area, a position of the measurement light 104 is not changed from that before the shielding because the measurement light 104 is condensed on a focal position of the eyeball optical system. The decrease in the luminance is solved by previously increasing an output of a light source of the measurement light 104. As a result, the aberration can be measured. Switching to the ring illumination is not limited to that in a configuration described in the present exemplary embodiment. For example, a light source of the ring illumination may be separately prepared. The change in the shape of the measurement light 104 is not limited to the change into the ring shape. The shape of the measurement light 104 may be any shape as long as the measurement light 104 has no portion to be irradiated onto the apex of the cornea.

According to the present exemplary embodiment, the subject's eye 109 having a wide pupil can also be aligned with the AO optical system with high-accuracy using reflected light at the apex of the cornea. Thus, the aberration can be measured with high-accuracy.

(Change in Irradiation Area)

Figure 8A:
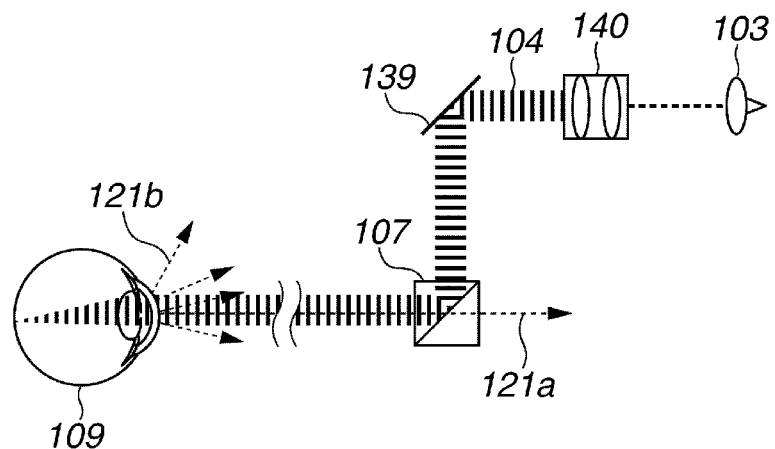
FIGS. 8A and 8B are schematic diagrams illustrating a change in an irradiation area in a subject's eye, which has been irradiated with measurement light, by an aberration measurement apparatus according to a third exemplary embodiment.
Figure 8B:
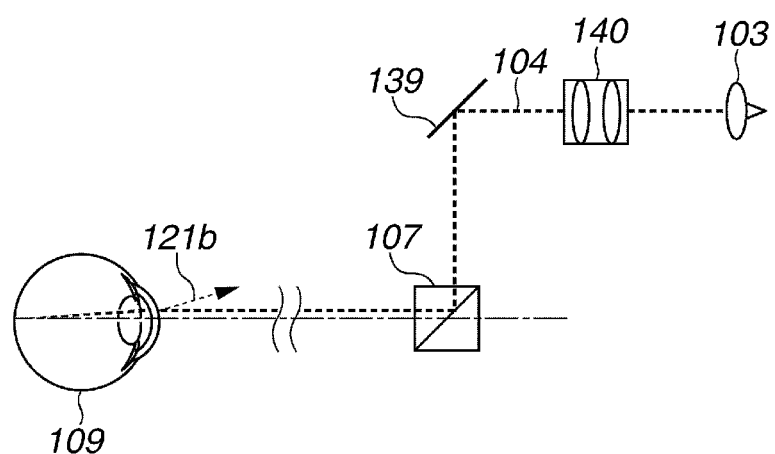

The third exemplary embodiment will be described below with reference to FIGS. 8A and 8B. FIGS. 8A and 8B are schematic diagrams illustrating a change in an irradiation area in a subject's eye 109, which has been irradiated with measurement light 104 by an aberration measurement apparatus according to the present exemplary embodiment. The present exemplary embodiment is an example in which cornea reflected light is controlled by changing the beam diameter of the measurement light 104. A configuration of the aberration measurement apparatus according to the present exemplary embodiment is similar to that in the first exemplary embodiment except for an irradiation portion with the measurement light 104.

A magnification mechanism 140 changes the beam diameter of the measurement light 104 that has been changed into parallel light by a collimator 103. The magnification mechanism 140 is an example of a diameter change unit configured to change the beam diameter of the measurement light 104. For example, the magnification mechanism 140 includes a plurality of lenses, is implemented by a configuration in which a positional relationship among the plurality of lenses is changed by inserting/removing into/from an optical system of the measurement light 104, and is driven by an actuator (not illustrated) or manually. The measurement light 104, which has been reflected on a fixed mirror 139, enters an optical path of a compensation optical system by a beam splitter 107, and is guided to the subject's eye 109. At this time, the beam splitter 107 and the fixed mirror 139 are arranged in the optical system so that an optical axis of the compensation optical system and an optical axis of the measurement light 104 are shifted by approximately 1 mm, for example.

As illustrated in FIG. 8A, in a process of alignment between the subject's eye 109 and the compensation optical system, the magnification mechanism 140 increases the beam diameter of the measurement light 104. At this time, even if the respective optical axes of the measurement light 104 and the compensation optical system are shifted, a part of the measurement light 104 covers the optical axis of the compensation optical system. Therefore, the apex of a cornea of the subject's eye 109 is included on the optical axis of the compensation optical system, cornea reflected light 121a of the measurement light 104, which has been reflected on the apex of the cornea, is mixed into the compensation optical system, and a bright spot is reflected in a wavefront sensor 113. Thus, the subject's eye 109 and the compensation optical system can be aligned with each other. In the present exemplary embodiment, a shift amount between the optical axis of the compensation optical system and the optical axis of the measurement light 104 is approximately 1 mm. Thus, the beam diameter of the measurement light 104 required for the alignment is 2 mm or more.

As illustrated in FIG. 8B, the magnification mechanism 140 reduces the beam diameter of the measurement light 104 to measure the aberration when the alignment is completed. Consequently, the measurement light 104 does not pass on the optical axis of the compensation optical system because the respective optical axes of the measurement light 104 and the compensation optical system are shifted. Therefore, the apex of the cornea is not irradiated with the measurement light 104. Thus, the cornea reflected light 121a also fades away, so that the bright spot disappears from the wavefront sensor 113. As a result, an aberration can be measured.

While the beam diameter change unit is the magnification mechanism 140 using a lens group in the present exemplary embodiment, it may be a unit for previously changing the measurement light 104 into thicker measurement light using the collimator 103 and using a diaphragm. However, in this case, the diaphragm decreases a light amount during measurement of an aberration. Thus, a laser output may be desirably set relatively high.

According to the present exemplary embodiment, alignment of a subject's eye having a wide pupil with an AO optical system can thus be performed with high-accuracy using reflected light on the apex of the cornea. Thus, the aberration can also be measured with high-accuracy.

Figure 9A:
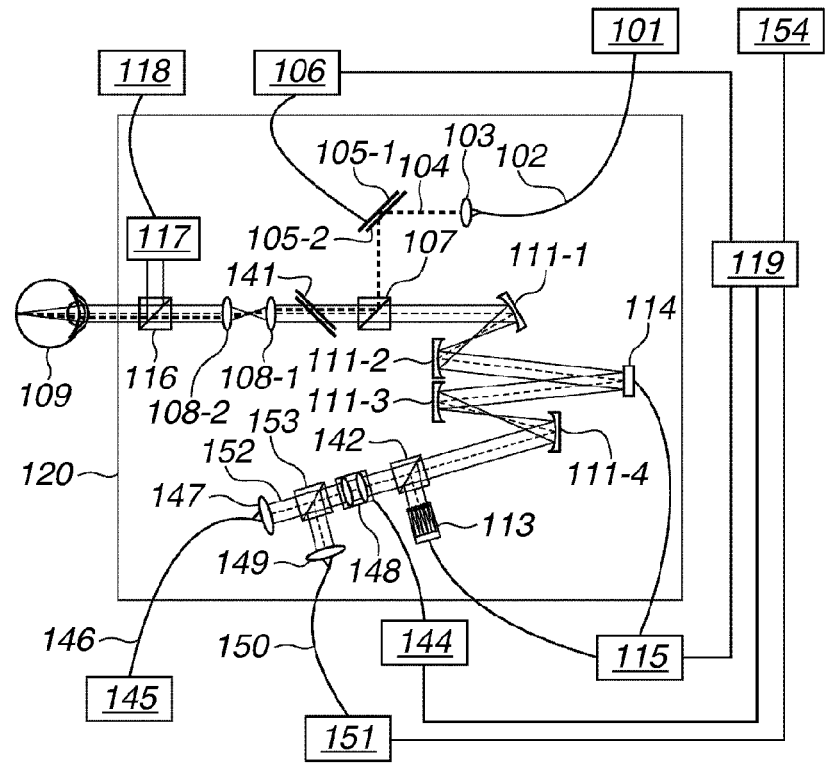
FIGS. 9A and 9B are schematic diagrams respectively illustrating aberration measurement apparatuses according to the fourth exemplary embodiment and a sixth exemplary embodiment.

An aberration measurement apparatus according to the fourth exemplary embodiment will be described with reference to FIG. 9A. FIG. 9A is a schematic diagram illustrating the aberration measurement apparatus according to the present exemplary embodiment. In FIG. 9A, the same reference numerals are assigned to the same components as those illustrated in FIG. 1, and hence description thereof is not repeated. In FIG. 9A, the movable mirror 105 illustrated in FIG. 1 includes movable mirrors 105-1 and 105-2.

The movable mirrors 105-1 and 105-2 are integrally movable in an optical axis direction. The movable mirrors 105-1 and 105-2 are configured so that the respective distances are changeable. For example, each of the movable mirrors 105-1 and 105-2 includes a movable stage and a beam steering. At this time, the movable mirror 105-1 reflects measurement light 104 from a light source in a direction perpendicular to a paper surface of the drawing. The movable mirror 105-2 reflects the measurement light 104 from the movable mirror 105-1 in a downward direction parallel to the paper surface. The movable mirror 105-2 is driven to move in a direction perpendicular to the paper surface with respect to the movable mirror 105-1 so that an irradiation position in the direction perpendicular to the paper surface can be adjusted with respect to the subject's eye 109. A reflection direction of cornea reflected light of the measurement light 104 can be controlled (described below). A mechanism for adjusting an irradiation position of the subject's eye 109 with the measurement light 104 is not limited to the above-mentioned configuration. For example, the mechanism can also be implemented by making the measurement light to be emitted from a collimator 103 thick and passing the thick measurement light through a pinhole that is movable in a biaxial direction. For example, the mechanism can also be configured by combining a single-axis movable mirror and an image rotator. A driving mechanism 106 for each of the movable mirrors 105-1 and 105-2 includes a biaxial direct acting shaft implemented by a motor and a ball screw, for example.

(Change in Visual Axis and Change in Irradiation Position)

A method for changing the irradiation position of the subject's eye 109 with the measurement light 104 according to the present exemplary embodiment will be described below with reference to FIGS. 10A to 10F.

Figure 10A:
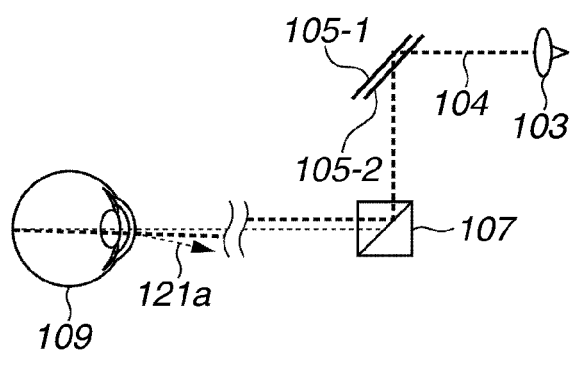
FIGS. 10A to 10F are schematic diagrams illustrating a change in an irradiation position of a subject's eye, which has been irradiated with measurement light, by the aberration measurement apparatus according to the fourth exemplary embodiment.
Figure 10B:
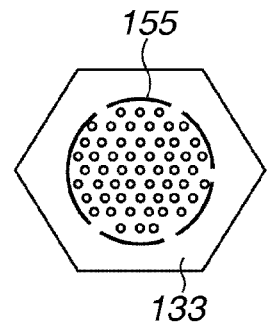

As illustrated in FIG. 10A, the irradiation position with the measurement light 104 is adjusted so that a position shifted from an eye axis of the subject's eye 109 (an optical axis of the subject's eye 109) is irradiated with the measurement light 104. At this time, the movable mirrors 105-1 and 105-2 are moved so that the wavefront sensor 113 does not receive cornea reflected light 121a, to adjust the irradiation position with the measurement light 104. Through this adjustment, as illustrated in FIG. 10B, the circular light portion 155 corresponding to a pupil of the subject's eye 109, in which a bright spot is not reflected, can be acquired by the CCD sensor 133 in the wavefront sensor 113.

Figure 10C:
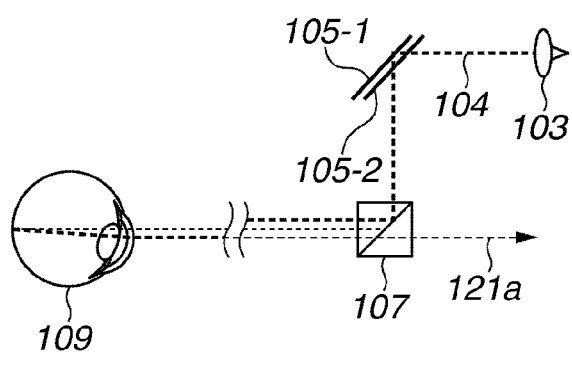
Figure 10D:
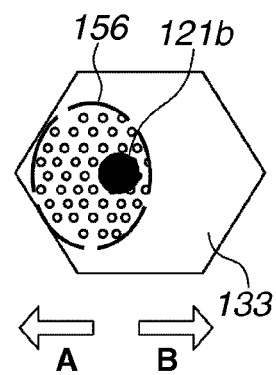

As illustrated in FIG. 10C, if a visual axis of the subject's eye 109 (a line of sight of the subject's eye 109) is changed, the cornea reflected light 121a may be receivable in the wavefront sensor 113. At this time, as illustrated in FIG. 10D, in a video picture based on a light receiving result of the wavefront sensor 113, a bright spot 121b (also referred to as a cornea reflected bright spot image) is reflected in an elliptical light portion 156 corresponding to the pupil of the subject's eye 109. When an aberration of the subject's eye 109 is measured in this state, the precision of the measurement of the aberration is deteriorated because the intensity of the bright spot 121b is high. The elliptical light portion 156 appears at a position of the CCD sensor 133 based on the visual axis of the subject's eye 109.

Figure 10E:
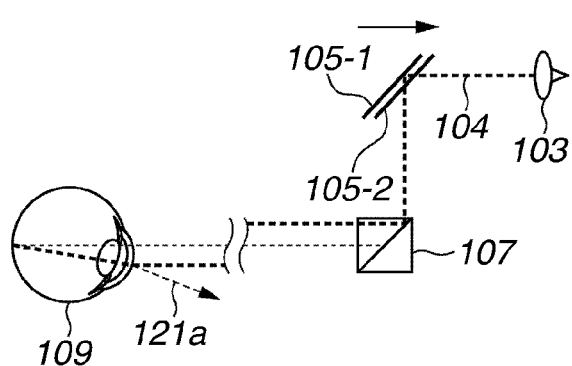
Figure 10F:
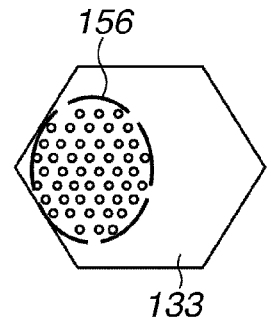

Therefore, as illustrated in FIG. 10E, the movable mirror 105-1 is moved in a direction indicated by an arrow. Thus, the irradiation position with the measurement light 104 can be moved toward a pupil center of the subject's eye 109. As illustrated in FIG. 10F, the irradiation position with the measurement light 104 can be adjusted so that the cornea reflected light 121a is not received by the wavefront sensor 113. A movement amount of the measurement light 104 is sufficient if it is approximately 0.5 to 1.0 mm with respect to the subject's eye 109.

As illustrated in FIG. 10D, if the video picture based on the light receiving result of the wavefront sensor 113 is displayed on a display unit, a user can know a positional relationship between the elliptical light portion 156 and the bright spot 121b. At this time, as illustrated in FIG. 10D, a display format representing a direction in which the bright spot 121b is desired to be moved with respect to the elliptical light portion 156 may be displayed on the display unit, as indicated by an arrow A and an arrow B, and the user may make the display format selectable. The user can move the movable mirror 105-1 in a rightward direction of the paper surface (a direction indicated by the arrow illustrated in FIG. 10E) by selecting the arrow A. Through this operation, the irradiation position with the measurement light 104 can be adjusted so that the cornea reflected light 121a is not received in the wavefront sensor 113, as described above. If the user selects the arrow B, the movable mirror 105-1 is moved in a leftward direction of the paper surface. However, in this case, the bright spot 121b may deviate from the elliptical light portion 156. The elliptical light portion 156 corresponds to the pupil of the subject's eye 109. If the bright spot 121b deviates from the elliptical light portion 156, the measurement light 104 may be vignetted by an iris of the subject's eye 109. Therefore, the user may preferably select the arrow A. The selection of the arrow is not limited to manual selection by the user. The selection of the arrow can also be automated. In this case, the movable mirror 105-1 may preferably be controlled so that the bright spot 121b moves in a direction indicated by the arrow A with respect to the elliptical light portion 156.

(Method for Controlling Aberration Measurement Apparatus)

Figure 11:
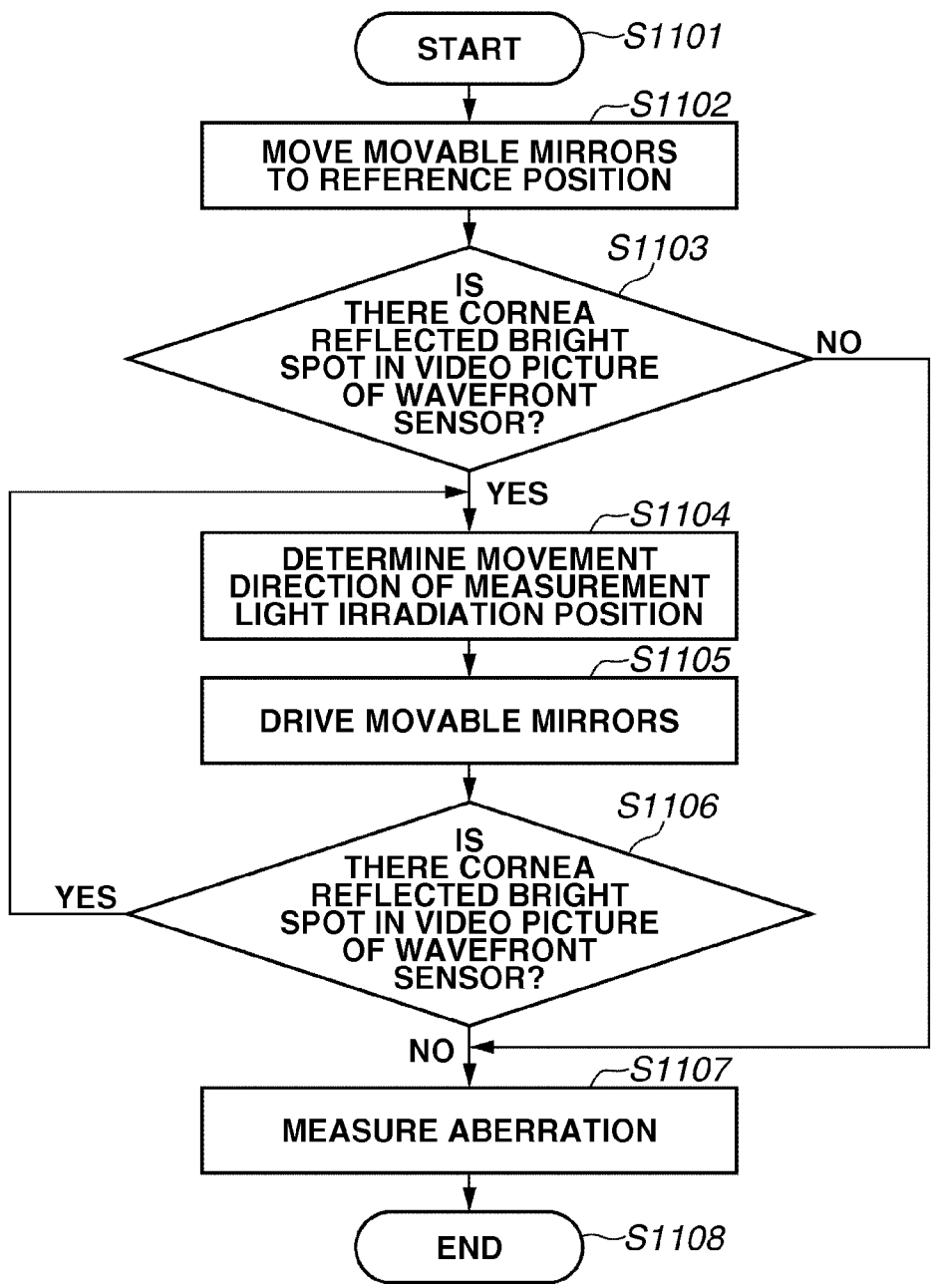
FIG. 11 is a flowchart illustrating a method for controlling the aberration measurement apparatus according to the fourth exemplary embodiment.

A method for controlling the aberration measurement apparatus according to the present exemplary embodiment will be described below with reference to a flowchart of FIG. 11 and a block diagram of FIG. 6B. In step S1101, a control start unit (not illustrated) starts to control the aberration measurement apparatus according to the present exemplary embodiment. If a measurement result of the aberration measurement apparatus is used when the subject's eye 109 and the aberration measurement apparatus are aligned with each other, the control of the aberration measurement apparatus is started before the alignment is performed. After another unit using a pupil of the subject's eye 109 performs the alignment, the control of the aberration measurement apparatus may be started. After rough alignment is performed by using the pupil of the subject's eye 109, fine alignment using the measurement result of the aberration measurement apparatus may be performed.

In step S1102, a mirror driving control unit 1601 then controls the driving mechanism 106, to move the movable mirrors 105-1 and 105-2 to a reference position (e.g., an origin position, or a previously defined coordinate position). Thus, the irradiation position of the subject's eye 109 with the measurement light 104 can be reset. If the current irradiation position is the reference position, the step S1101 need not be performed.

In step S1103, a cornea reflected bright spot presence/absence determination unit 1602 determines the presence or absence of a cornea reflected bright spot based on a light receiving result of the wavefront sensor 113. Herein, the user can determine the presence or absence of the cornea reflected bright spot while seeing a video based on the light receiving result of the wavefront sensor 113. The control unit 119 can also automatically determine that the cornea reflected bright spot exists if an output of the wavefront sensor 113 is a threshold value or larger. If the cornea reflected bright spot does not exist (NO in step S1103), the processing proceeds to step S1107. In step S1107, the compensation optical control unit 115 controls the wavefront sensor 113, to measure an aberration. If the cornea reflected bright spot exists (YES in step S1103), the processing proceeds to step S1104. In step S1104, a movement direction determination unit 1603 determines a direction in which the irradiation position with the measurement light 1104 is moved (a movement direction) from a positional relationship between the cornea reflected bright spot and a light portion corresponding to the pupil of the subject's eye 109 based on the light receiving result of the wavefront sensor 113. The determination may be performed while the user sees the video picture based on the light receiving result of the wavefront sensor 113, or may be automatically performed by the control unit 119.

In step S1105, the mirror driving control unit 1601 controls the driving mechanism 106 according to a determination result of the movement direction determination unit 1603, to drive the movable mirrors 105-1 and 105-2. A driving amount may be a fixed value, or may be designable by the user. If the driving of the movable mirrors 105-1 and 105-2 is completed, the processing proceeds to step S1106. In step S1106, the cornea reflected bright spot presence/absence determination unit 1602 determines the presence or absence of the cornea reflected bright spot again. If the cornea reflected bright spot does not exist (NO in step S1106), the processing proceeds to step S1107. In step S1107, a compensation optical control unit 115 controls the wavefront sensor 113, to measure the aberration. If the cornea reflected bright spot still exists (YES in step S1106), the processing returns to step S1104. If the aberration has been measured in step S1107, the processing proceeds to step S1108. In step S1108, a control end unit (not illustrated) ends the control of the aberration measurement apparatus according to the present exemplary embodiment.

Through these operations, a good irradiation position, which is not affected by the cornea reflected bright spot or vignetting (shielding) by the iris, can efficiently be irradiated with the measurement light 104. Thus, a period of time required to measure the aberration can be shortened, and therefore, a burden on a subject can be reduced. When the user moves the irradiation position with the measurement light 104, if a display control unit (not illustrated) included in the control unit 119 displays a movement direction, together with the video picture based on the light receiving result of the wavefront sensor 113, on a display unit such as a display 154, operability of the user can be improved.

Figure 12B:
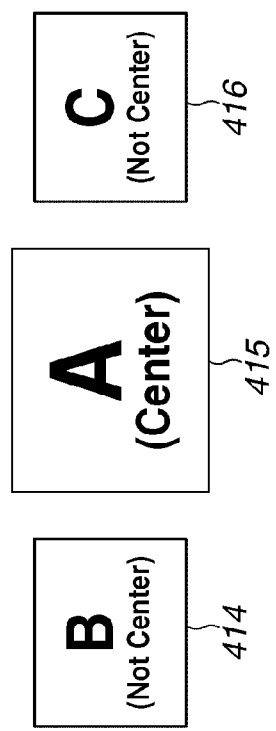
FIG. 12B is a schematic diagram illustrating a position correction execution button according to a seventh exemplary embodiment.
Figure 12A:
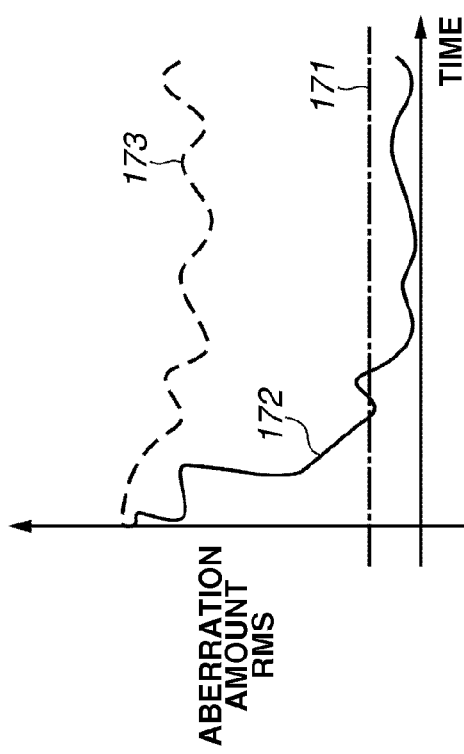
FIG. 12A is a graph representing a change in an aberration amount with a period of time elapsed since measurement of an aberration of a subject's eye was started (or the number of times of correction of the aberration) by an aberration measurement apparatus according to a fifth exemplary embodiment.

An aberration measurement apparatus according to the fifth exemplary embodiment will be described below with reference to FIG. 12A. FIG. 12A is a graph representing a change in an aberration amount with a period of time elapsed since the aberration measurement apparatus according to the present exemplary embodiment started to measure an aberration of a subject's eye 109 (or the number of times of correction of the aberration). A configuration of the aberration measurement apparatus according to the present exemplary embodiment is similar to that in the fourth exemplary embodiment. A user can recognize an irradiation state of the subject's eye 109 with measurement light 104 based on an aberration correction result using the aberration measurement apparatus according to the present exemplary embodiment. More specifically, the user can determine the presence or absence of a cornea reflected bright spot in a video picture based on a light receiving result of a wavefront sensor 113. The present exemplary embodiment is a method effective for a case where a correction amount is continuously calculated for a plurality of ranges of the subject's eye 109 when the aberration is measured and corrected.

First, a calculation unit (not illustrated) included in a compensation optical control unit 115 models a wavefront, which has been acquired from the wavefront sensor 113, on a Zernike function, to calculate a coefficient related to each degree. The calculation unit then calculates a modulation amount based on the calculated coefficient. The compensation optical control unit 115 controls a wavefront correction device 114 based on the calculated modulation amount.

Generally, in a single aberration measurement and aberration correction, correction to a wavefront having a low aberration is not easy to perform. The aberration is repeatedly measured and corrected until an aberration amount of a correction residual becomes an aberration amount 172 in which the subject's eye 109 can be imaged. If the correction is correctly performed, the aberration amount decreases with an increase in the number of times of correction. The aberration amount of the correction residual becomes less than a predetermined aberration amount 171 required to acquire an SLO image.

On the other hand, if the wavefront sensor 113 is irradiated with cornea reflected light 121a obtained by reflecting the measurement light 104 on a cornea of the subject's eye 109 as stray light, a bright spot 121b is captured in the wavefront sensor 113, as illustrated in FIG. 10C. If the aberration is corrected in this state, the correction amount cannot be correctly calculated because the intensity of the bright spot 121b is high. Thus, the correction residual is not converged, like when the aberration amount of the correction residual is an aberration amount 173. Therefore, determination of a failure in the correction of the aberration based on a limited time (or a limited number of times) elapsed until the correction residual is converged enables determination whether the bright spot 121b is captured by the CCD sensor 133.

Control of the aberration measurement apparatus (or an aberration correction apparatus) according to the present exemplary embodiment will be described with reference to a flowchart of FIG. 13. The same steps as those illustrated in FIG. 11 described in the fourth exemplary embodiment are assigned the same step numbers. Different steps from those illustrated in FIG. 11 will be described below.

After step S1102, in step S1201, the compensation optical control unit 115 controls the wavefront sensor 113 and the wavefront correction device 114, to measure and correct an aberration, and the processing proceeds to step S1202. In step S1202, an aberration determination unit (not illustrated) determines whether a correction residual is converged (e.g., an aberration amount becomes less than a predetermined amount) within a predetermined period of time (or a predetermined number of times of correction). If the correction residual is converged (YES in step S1202), the processing proceeds to step S1108. In step S1108, a control end unit (not illustrated) ends the control of the aberration measurement apparatus according to the present exemplary embodiment. If the correction residual is not converged (NO in step S1202), the processing proceeds to step S1103. Steps S1103 to S1106 are similar to those in the fourth exemplary embodiment. If there is no cornea reflected bright spot (NO in step S1106), the processing proceeds to step S1203. In step S1203, the compensation optical control unit 115 controls the wavefront sensor 113 and the wavefront correction device 114, to measure and correct the aberration. Thus, the presence or absence of the cornea reflected bright spot can be determined in a process of measuring and correcting the aberration. Therefore, as long as there is no cornea reflected bright spot image, a period of time required to determine the presence or absence of a cornea reflected bright spot image can be saved. Therefore, a period of time required to correct the aberration can be shortened, and therefore, a burden on a subject can be reduced.

Figure 9B:
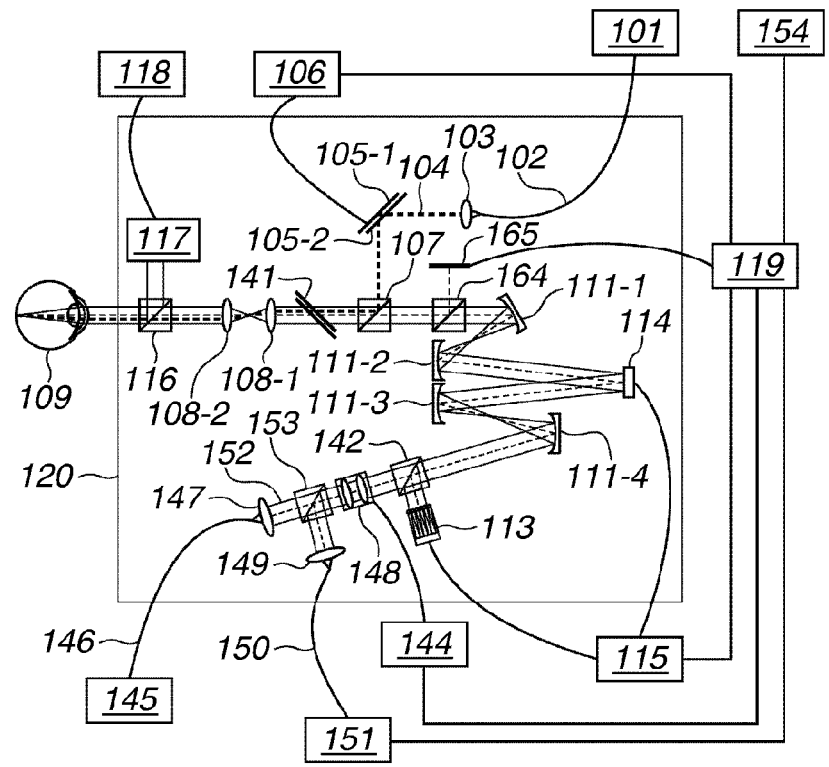

A sixth exemplary embodiment will be described below with reference to FIG. 9B. FIG. 9B is a schematic diagram illustrating a configuration of an aberration measurement apparatus according to the present exemplary embodiment. In the present exemplary embodiment, an irradiation state with measurement light 104 is determined based on a lighting position of a fixation lamp (a fixation target position). In the aberration measurement apparatus according to the present exemplary embodiment, an SLO with a compensation optical function illustrated in FIG. 9B is provided with a beam splitter 164 and a fixation lamp 165, and a subject's eye 109 is irradiated with fixation display of the fixation lamp 165 via the beam splitter 164. The fixation lamp 165 uses a display (a fixation display unit) on which any fixation target can be displayed by liquid crystal display. A fixation lamp control unit (not illustrated) included in a control unit 119 controls the fixation lamp 165. The fixation display unit of the fixation lamp 165 can also be implemented by a plurality of light sources.

Figure 14A:
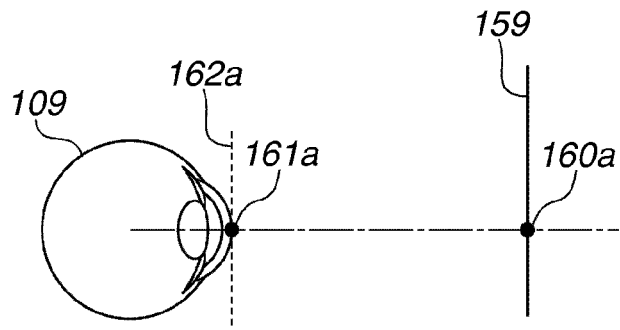
FIGS. 14A to 14C are schematic diagrams illustrating a visual axis of a subject's eye and a mirror surface reflection position in the aberration measurement apparatus according to the sixth exemplary embodiment.
Figure 14B:
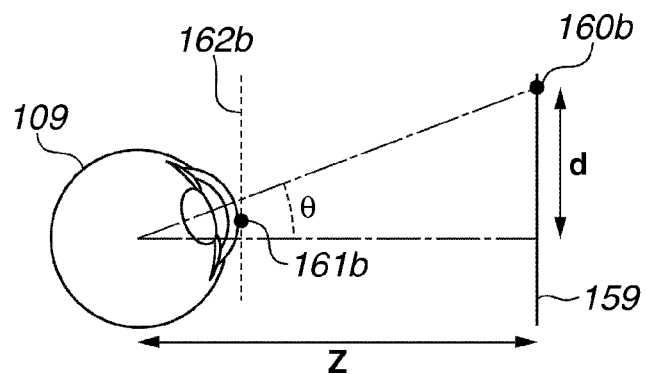
Figure 14C:
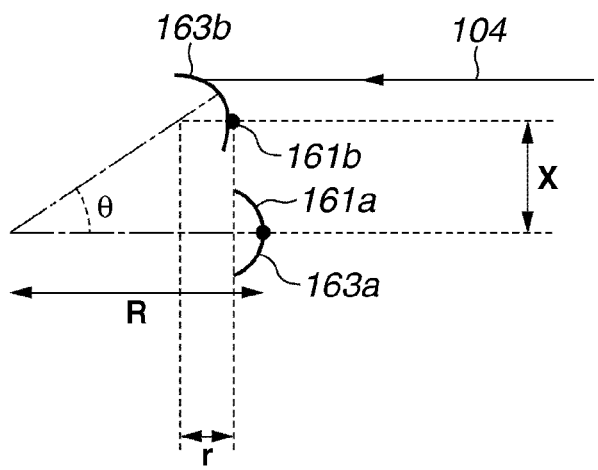

How a visual axis of the subject's eye 109 is changed depending on the fixation target position will be described with reference to FIGS. 14A to 14C. FIG. 14A illustrates a conjugate position 159 of the fixation lamp 165 as viewed from the subject's eye 109, and displayed targets 160a and 160b. In FIG. 14A, the target 160a is positioned at the center of an optical axis of an optical system, and an eye axis of the subject's eye 109, which has fixated the target 160a, substantially matches the optical axis of the optical system. At this time, a plane 162a out of planes contacting a surface of a cornea of the subject's eye 109 vertically contacts the optical axis at a contact 161a. The contact 161a substantially matches the apex of the cornea. When the contact 161a is irradiated with measurement light 104, cornea reflected light is mixed into a wavefront sensor 113. FIG. 14B illustrates a case where the target 106b has been shifted by a distance d from a position of the optical axis of the optical system. An eye axis of the subject's eye 109, which has fixated the target 106b, forms an angle of θ with the optical axis of the optical system. A distance Z from a rotation center of a pupil of the subject's eye 109 when the subject's eye 109 changes its line of sight to the conjugate position 159 of the fixation lamp 165 is $\theta = \tan^{-1}(d/z)$. A plane 162b out of the planes contacting the surface of the cornea of the subject's eye 109 vertically contacts the optical axis at a contact 161b. The contact 161b is also irradiated with the measurement light 104 so that cornea reflected light is received in the wavefront sensor 113. When a position of the contact 161b is calculated from the distance d, the cornea reflected light is received in the wavefront sensor 113. Thus, an irradiation position of the subject's eye 109 with the measurement light 104 can be determined. A calculation method therefor will be described with reference to FIG. 14C. Corneas 163a and 163b of the subject's eye 109 are respectively at a position where the target position 160a has been fixated and a position where the target position 160b has been fixated. A distance X between the contact 161b and the optical axis of the optical system is obtained by $X=(R-r)\cos\theta$, wherein R is a distance from the rotation center of the pupil to the apex of the cornea when the subject's eye 109 changes the line of sight and r is a radius of curvature when the cornea is regarded as a spherical surface. The irradiation position with the measurement light 104 is determined by avoiding a stray light generation position obtained by the foregoing. A position of the pupil moves with a change in the line of sight. Thus, the measurement light 104 may be shifted in a direction away from the optical axis of the optical system. FIG. 14C illustrates a good irradiation position of the cornea 163b with the measurement light 104. A shift amount may be approximately 0.5 to 1.0 mm from the stray light generation position, like in the fourth exemplary embodiment.

Control of the aberration measurement apparatus (or the aberration correction apparatus) according to the present exemplary embodiment will be described below with reference to a flowchart of FIG. 15. The same steps as those illustrated in FIGS. 11 and 13, described in the fourth and fifth exemplary embodiments, are assigned the same step numbers. Different steps from those illustrated in FIGS. 11 and 13 will be described below. In step S1301, a fixation lamp control unit (not illustrated) lights a predetermined position of the fixation lamp 165 (displays the predetermined position at the target position). In step S1302, an irradiation position determination unit (not illustrated) determines an irradiation position with the measurement light 104 based on a lighting position of the fixation lamp 165. Thus, a good irradiation position, which is not affected by a cornea reflected bright spot or vignetting (shielding) by an iris of the subject's eye 109, can be irradiated with the measurement light 104. Thus, a period of time required to measure an aberration can be shortened, and therefore, a burden on a subject can be reduced.

A method for adjusting respective positions of a subject's eye 109 and an ophthalmologic apparatus (particularly, an optical system 120) according to the seventh exemplary embodiment will be described below with reference to FIGS. 16A and 16B. An aberration measurement apparatus according to the present exemplary embodiment is similar to that in the first exemplary embodiment, and hence description thereof is not repeated.

An optical system 120 can be moved in three directions, i.e., in up-and-down, right-and-left, and back-and-forth directions when an operator manually operates a joystick (not illustrated). The operator operates the joystick while confirming a video picture of an anterior eye of the subject's eye 109, which has been captured by an anterior eye observation camera 117, using a monitor 118, to roughly adjust a position of the optical system 120 with respect to the subject's eye 109. A face rest (not illustrated) for receiving the face of a subject can be driven in three directions, i.e., up-and-down, right-and-left, and back-and-forth directions when a control unit 119 controls a motor (not illustrated). After the position of the optical system 120 is roughly adjusted with respect to the subject's eye 109 using the joystick, the face rest is driven, as needed, to finely adjust a position of the subject's eye 109 with respect to the optical system 120. An operator inputs driving of the face rest to the control unit 119 using an input device (not illustrated), which is implemented by a mouse and a keyboard.

Figure 16A:
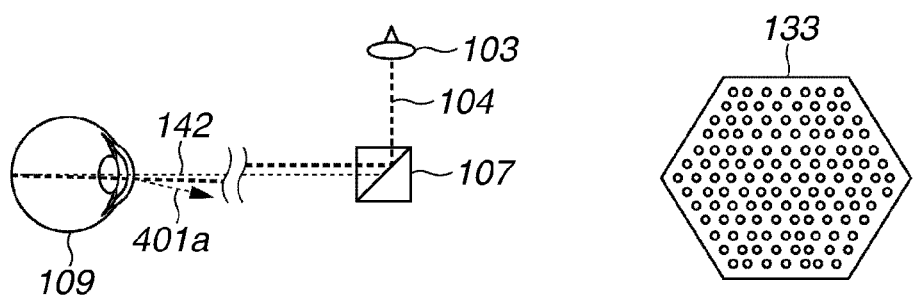
FIGS. 16A and 16B are schematic diagrams illustrating generation of a cornea reflected bright spot image according to the seventh exemplary embodiment.
Figure 16B:
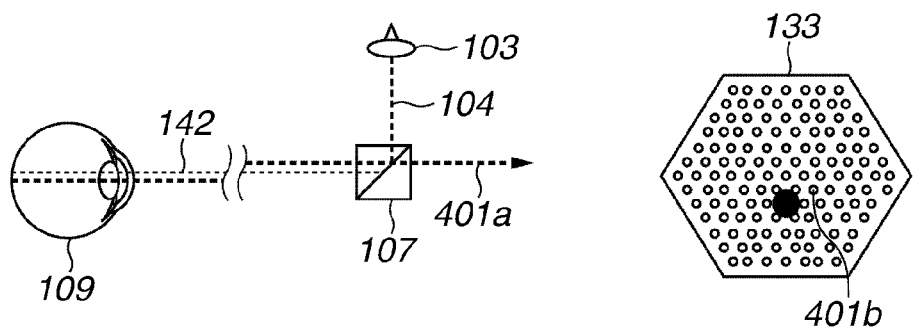

FIG. 16A illustrates a case where an optical axis 402 of the optical system 120 and an eye axis of the subject's eye 109 match each other and are in a correct positional relationship. Cornea reflected stray light 401 is obtained by mirror surface-reflecting measurement light 104 on a surface of a cornea of the subject's eye 109. To avoid the cornea reflected stray light 401 being mixed into a compensation optical system, the measurement light 104 is shifted from an optical axis of the compensation optical system, and is adjusted to be irradiated 0.5 to 1 mm below the center of the subject's eye 109 in the present exemplary embodiment. In this case, a wavefront sensor 113 can satisfactorily observe reflected and scattered light from a retina of the subject's eye 109. If the respective positions of the subject's eye 109 and the optical system 120 are unsuccessfully adjusted so that an optical axis of the measurement light 104 and an optical axis of the subject's eye 109 match each other, as illustrated in FIG. 16B, however, a part of the measurement light 104 is regularly reflected on the cornea of the subject's eye 109 and is mixed into the compensation optical system. In this case, cornea reflected stray light 401a is guided to the wavefront sensor 113, and a cornea reflected bright spot image 401b, which is brighter than the others, is reflected in a CCD sensor 133 by receiving the cornea reflected stray light 401a. While the cornea reflected bright spot image 401b is reflected, correct wavefront measurement cannot be performed. Therefore, the positions of the subject's eye 109 and the optical system 120 need to be returned to a correct positional relationship.

A pupil of the subject's eye 109 and the wavefront sensor 113 are arranged to be conjugate with each other. Thus, a spot group to be reflected in the CCD sensor 133 corresponds to a real image of an anterior eye of the subject's eye 109. Therefore, the cornea reflected bright spot image 401b represents a position on the cornea where the regular reflection occurs. If the subject's eye 109 fixates the front, as illustrated in FIG. 16B, the cornea reflected bright spot image 401b represents a position at the apex of the cornea because the regular reflection occurs at the apex of the cornea. In the present exemplary embodiment, the center of the wavefront sensor 113 and the optical axis of the compensation optical system are matched. Therefore, matching between the position at the apex of the cornea and the center of the CCD sensor 133 is a correct positional relationship between the optical system 120 and the subject's eye 109. From a direction and a distance from the center of the CCD sensor 133 to the cornea reflected bright spot image 401b, a correction amount for correcting the above-mentioned positional relationship is determined. The control unit 119 calculates the correction amount based on an image of the wavefront sensor 113, and notifies the operator of mixing of stray light using the monitor 118. The control unit 119 prompts the operator to determine whether the above-mentioned positional relationship is to be changed using a motor for driving the face rest.

For example, three buttons are displayed on the monitor 118. The operator can determine whether the positional relationship is to be changed by selecting one of the buttons and pressing the selected button. A schematic diagram of the displayed buttons is illustrated in FIG. 12B. When an A button 415 is pressed, position correction driving is performed so that a positional relationship between the optical system 120 and the subject's eye 109 becomes correct. A B button 414 and a C button 416 correspond to a case where the positional relationship between the optical system 120 and the subject's eye 109 is desired to be changed from a predetermined positional relationship to avoid turbidity caused by a cataract. If there is a turbidity portion in the subject's eye 109 due to the cataract, the subject's eye 109 and the ophthalmologic apparatus may be aligned with each other to avoid the turbidity portion. In this case, the alignment is performed to avoid the turbidity portion of the subject's eye 109. Further, an irradiation position where the measurement light 104 is reflected in a direction different from a direction toward the sensor on the surface of the cornea is desired to be determined. At this time, when the B button 414 is pressed, an optical axis of the optical system 120 is changed to a position 1.5 mm leftward from the center of the subject's eye 109. When the C button 416 is pressed, the optical axis is similarly changed to a position 1.5 mm rightward therefrom.

Figure 17C:
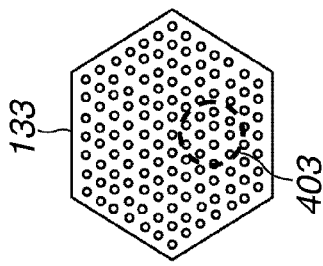
FIGS. 17A to 17F are schematic diagrams illustrating a positional relationship among measurement light, a subject's eye, a bright spot image, and a wavefront sensor according to the seventh exemplary embodiment.
Figure 17B:
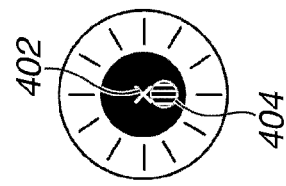
Figure 17A:
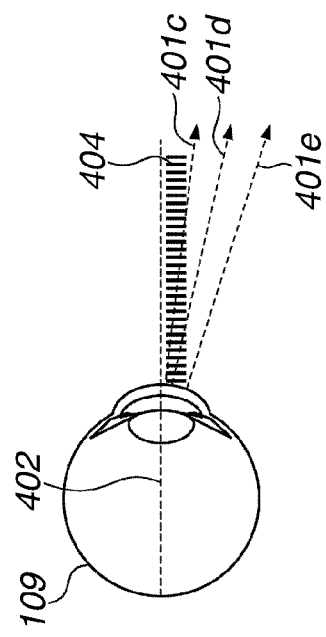

The measurement light 104 has a predetermined thickness. In the present exemplary embodiment, the measurement light 104 has a beam diameter of approximately 0.8 mm on the cornea of the subject's eye 109. The beam diameter is not particularly defined to this value. If the beam diameter is too large, the cornea reflected stray light 401a is easily mixed into the compensation optical system. FIGS. 17A to 17C illustrate a case where a positional relationship between the subject's eye 109 and the compensation optical system is correct. In FIG. 17A, an optical axis 402 of the compensation optical system matches the center of the subject's eye 109. If measurement light 104 having a predetermined thickness is mirror surface-reflected on a spherical surface of the cornea of the subject's eye 109, the measurement light 104 travels while spreading downward, as indicated by arrows 401c to 401e. FIG. 17B illustrates how an iris of the subject's eye 109 at this time is viewed from the front. While the measurement light 104 is irradiated in a range 404, the cornea reflected stray light 401a does not return to the compensation optical system. Therefore, in this case, the cornea reflected stray light 401a is not reflected in a video picture of the anterior eye observation camera 117 or a CCD video picture of the wavefront sensor 113 illustrated in FIG. 17C. In FIG. 17C, a range 403 enclosed by a broken line corresponds to a cornea surface portion that is irradiated with the measurement light 104.

Figure 17F:
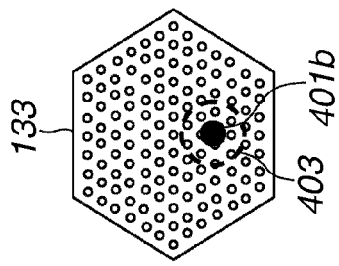
Figure 17E:
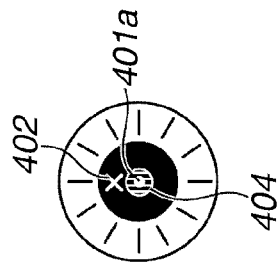
Figure 17D:
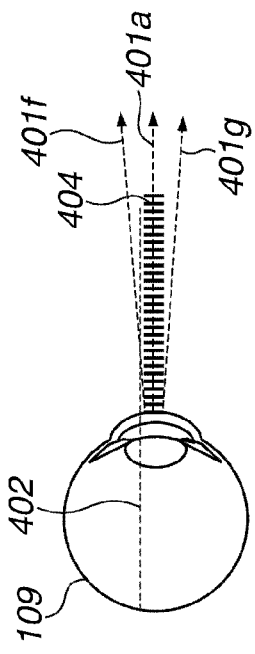

The cornea reflected bright spot image 401b can occur in the range 403. FIG. 17D to FIG. 17F illustrate how the cornea reflected bright spot image 401b is reflected when the apex of the cornea is positioned in the range 403. The optical axis 402 of the compensation optical system is shifted upward from the center of the subject's eye 109, and a range including the apex of the cornea of the subject's eye 109 is irradiated with the measurement light 104. The measurement light 104, which has been regularly reflected on the apex of the cornea, serves as the cornea reflected stray light 401a, to form the cornea reflected bright spot image 401b in the CCD video picture of the wavefront sensor 113. The cornea reflected bright spot image 401b is formed within the range 403.

The range 403 is uniquely determined as the compensation optical system. Thus, accuracy of occurrence of the correction driving can be improved by limiting a detection coverage of the cornea reflected bright spot image 401b to the range 403. From an intensity distribution of the measurement light 104, the intensity of the cornea reflected bright spot image 401b has a substantially Gaussian distribution in the range 403. Therefore, accuracy of detection of the cornea reflected bright spot image 401b can also be improved by changing a threshold intensity level of the detection depending on a position. If a light amount of the measurement light 104 can be controlled, the light amount may also be used to determine the threshold intensity level.

Figure 18:
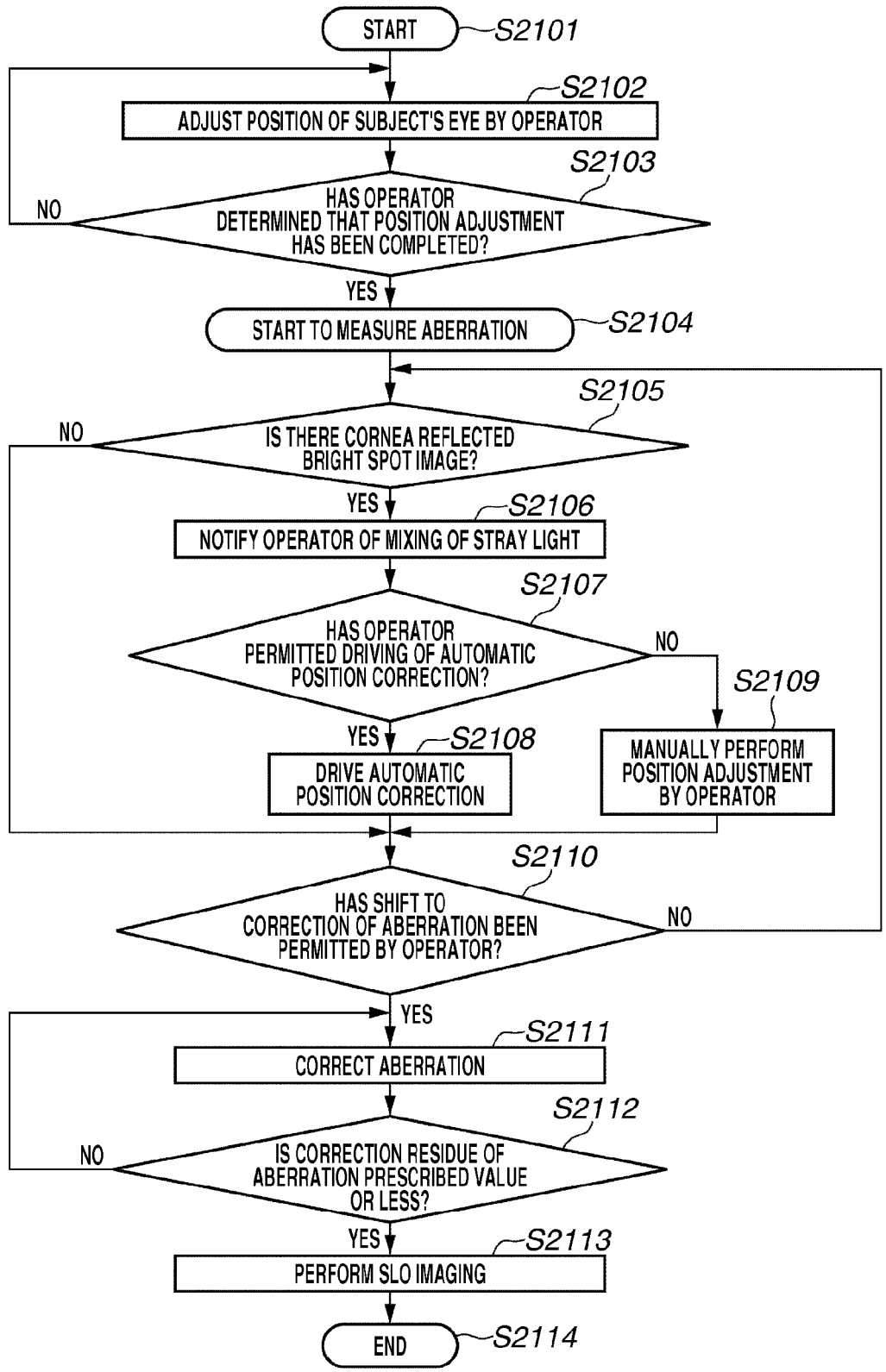
FIG. 18 is a flowchart illustrating an example of control steps according to the seventh exemplary embodiment.

The flow of the measurement in the present exemplary embodiment will be described below with reference to a flowchart of FIG. 18. In step S2101, the control unit 119 starts the measurement. In step S2102, the control unit 119 performs position adjustment based on a video of an anterior eye of the subject's eye 109. The position adjustment is performed by operating a driving mechanism for the optical system 120 using the joystick so that a pupil of the subject's eye 109 is aligned with and focused on the center of the monitor 118 while confirming a video picture of the anterior eye observation camera 117 using the monitor 118. In addition to a position adjustment method according to the present exemplary embodiment, a method for overlaying an alignment target for guiding some of features of the anterior eye on the monitor 118 and displaying the overlaid alignment target may be used. In step S2102, an operator may issue an instruction to a motor for driving the face rest, as needed, to perform fine adjustment. In step S2103, the operator determines whether the position adjustment has been completed. In the present exemplary embodiment, the operator performs the determination. However, the ophthalmologic apparatus may automatically perform the determination using image information processing performed by the control unit 119. If the operator determines that the position adjustment has been completed (YES in step S2103), the control unit 119 switches the ophthalmologic apparatus to an aberration measurement mode using the input device. In step S2104, the control unit 119 starts to measure an aberration of the subject's eye 109. In step S2105, the control unit 119 determines whether a cornea reflected bright spot image has been detected. In the determination, the control unit 119 detects the cornea reflected bright spot image depending on a threshold value for detecting the bright spot image according to a position of the bright spot image and a dimming level of the measurement light 104, as described above. If the bright spot image has not been detected (NO in step S2105), the processing proceeds to step S2110. In step S2110, the control unit 119 prompts the operator to start to correct the aberration. If the bright spot image has been detected (YES in step S2105), the processing proceeds to step S2106. In step S2106, the control unit 119 notifies the operator of mixing of stray light, to determine whether automatic position correction is to be performed.

In step S2107, the control unit 119 determines whether driving of the automatic position correction has been permitted by the operator through the input unit. If the driving of the automatic position correction has been permitted (YES in step S2107), then in step S2108, the control unit 119 performs the driving. If the driving of the automatic position correction has not been permitted (NO in step S2107), then in step S2109, the operator manually performs the position adjustment again. In step S2110, the operator determines whether the aberration of the subject's eye 109 is normally measured, and shift to correction of the aberration may be permitted. If the operator determines that the shift to the correction of the aberration is to be permitted, and inputs the permission to the input unit (YES in step S2110), the processing proceeds to step S2111. In step S2111, the control unit 119 corrects the aberration. In step S2112, the control unit 119 determines whether a correction residual of the aberration is a predetermined value or less. If the control unit 119 determines that the correction residual of the aberration is the predetermined value or less (YES in step S2112), the processing proceeds to step S2113. In step S2113, the control unit 119 performs SLO imaging. In step S2114, the imaging ends.

According to the present exemplary embodiment, an additional member is not required, a case where cornea reflected stray light is mixed into an aberration measurement system can be quickly and accurately coped with, a measurement time can be shortened, and a burden on a subject can be reduced.

The eighth exemplary embodiment will be described below with reference to FIGS. 19A, 19B, 19C, and 19D. FIGS. 19A, 19B, 19C, and 19D are schematic diagrams illustrating a display pattern for avoiding stray light according to the present exemplary embodiment. In the present exemplary embodiment, the display pattern is used to allow an operator to set a correct irradiation position for the measurement by avoiding stray light. A configuration of an apparatus according to the present exemplary embodiment drives an apparatus body by operating a joystick instead of driving a face rest, to appropriately avoid cornea reflected stray light. At this time, a direction and an amount in which an irradiation position is to be changed are presented to the operator using a monitor 118.

Figure 19A:
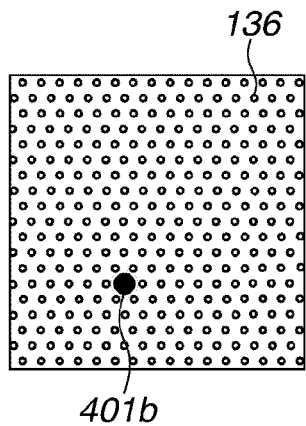
FIGS. 19A to 19D are schematic diagrams illustrating a display pattern for avoiding stray light according to the eighth exemplary embodiment.

FIG. 19A illustrates a case where a bright spot image 401b caused by the cornea reflected stray light has been reflected in a video picture of a CCD sensor 133. At this time, a control unit 119 calculates a position correction amount and a direction required for an optical system 120 based on the center of the CCD center 113 serving as the center of a compensation optical system and a distance and a direction of the cornea reflected bright spot image 401b. A control unit 119 displays any one of or one or more of display formats illustrated in FIGS. 19B to 19D and FIG. 12C on the monitor 118, to present a direction and an amount where an irradiation position is to be changed to the operator. The display is performed according to the presence or absence of the cornea reflected stray light, and is performed when the cornea reflected stray light has been detected.

Figure 19B:
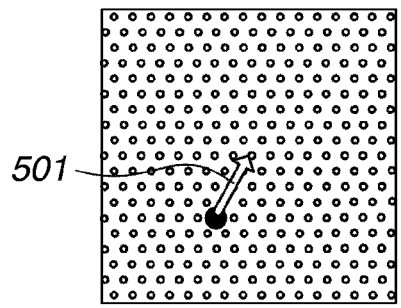

FIG. 19B illustrates the video picture of the CCD sensor 133. An arrow 501 is displayed on the video picture, to present a direction and an amount in which the joystick is to be operated to the operator. A starting point of the arrow 501 is a position of the bright spot image 401b, and an ending point of the arrow 501 is the center of the video picture of the CCD sensor 133 serving as the center of the compensation optical system. Since the position of the bright spot image 401b is a position at the apex of a cornea of a subject's eye, a schematic picture of an eyeball 506 may be overlapped and displayed thereon, as illustrated in FIG. 19D.

Figure 19C:
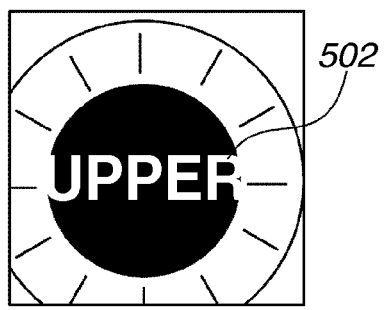
Figure 19D:
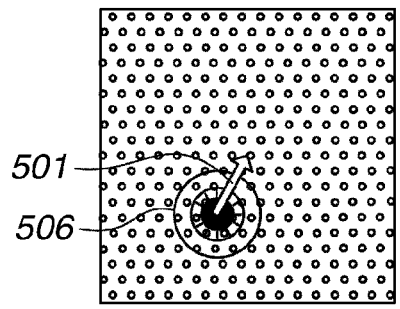

FIG. 19C illustrates a video picture of an anterior eye observation camera 117. A direction of position correction required to avoid stray light is indicated by characters "UPPER" 502 on the video picture.

Figure 12D:
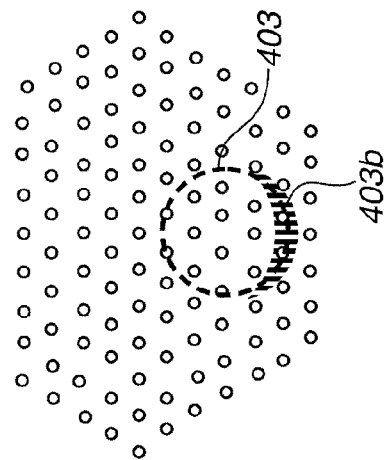
FIG. 12D is a schematic diagram illustrating a range in which a bright spot image is generated on a wavefront sensor according to the eighth exemplary embodiment.
Figure 12C:
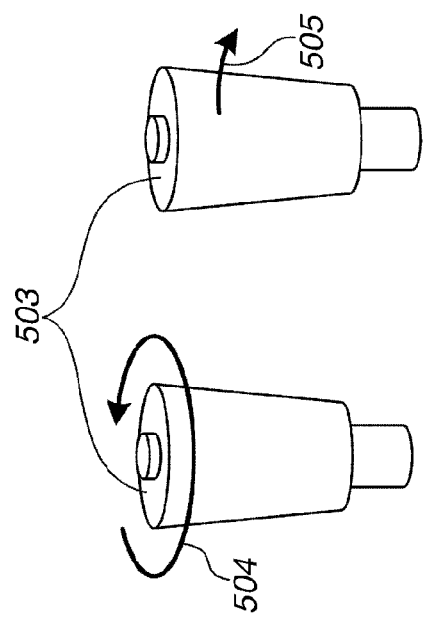
FIG. 12C is a schematic diagram illustrating display of an operation of a joystick according to an eighth exemplary embodiment.

In FIG. 12C, an operation to be given to a joystick 503 is illustrated by arrows 504 and 505. When the joystick 503 is tilted rightward or leftward, the optical system 120 moves rightward or leftward with respect to a subject. If the joystick 503 is rotated, the optical system 120 moves in a vertical direction. Means for guiding an operator to avoid the stray light may be voice in addition to the display.

In the present exemplary embodiment, the apparatus also has a function of notifying, if an operation direction by the operator for avoiding the stray light is not correct, that the operation direction of the operator is not correct. FIG. 12D illustrates a portion of a range 403 in the video picture of the CCD sensor 133 in an enlarged manner. A bright spot image generated in the range 403 moves upward within the range 403 if the operator correctly performs a correction operation, and disappears at the time point where it has gone out of the range 403. The bright spot image moves downward within the range 403 if the operator performs the correction operation in an opposite direction, and disappears after passing through a lower portion 403b of the range 403. If the bright spot image existing at a position of the lower portion 403b disappears immediately after it has gone out of the range 403, it is determined that the operator has performed the correction operation in an opposite direction, to perform display to suggest an error to the correction operation on the monitor 118.

According to the present exemplary embodiment, even if there is thus no actuator for adjusting a positional relationship between the subject's eye 109 and an aberration measurement system, a case where the cornea reflected stray light is mixed into the aberration measurement system can be quickly and accurately coped with, and a measurement time can be shortened.

ANOTHER EXEMPLARY EMBODIMENT

The present invention is also implemented by performing the following processing, i.e., processing for supplying software (a program) for implementing the functions of the above-mentioned exemplary embodiments to a system or an apparatus via a network or various storage media and causing a computer (or a central processing unit (CPU) or a microprocessing unit (MPU)) in the system or the apparatus to read out and execute the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-236798 filed Oct. 26, 2012, No. 2012-236797 filed Oct. 26, 2012, No. 2012-236799 filed Oct. 26, 2012, and No. 2013-181188 filed Sep. 2, 2013, which are hereby incorporated by reference herein in their entirety.

What is claimed is:

1. An ophthalmologic apparatus comprising:
    an aberration measurement unit configured to measure an aberration of a subject's eye;
    a positional relationship change unit configured to change a positional relationship between the subject's eye and an optical system including the aberration measurement unit in a first irradiation state of an anterior eye of the subject's eye with measurement light; and
    an irradiation state change unit configured to change an irradiation state of the anterior eye of the subject's eye with the measurement light from the first irradiation state to a second irradiation state for correcting the aberration of the subject's eye based on a measurement result of the aberration measurement unit.

2. The ophthalmologic apparatus according to claim 1, wherein the positional relationship change unit changes the positional relationship based on the measurement result of the aberration measurement unit.

3. The ophthalmologic apparatus according to claim 1,
    wherein the aberration measurement unit measures a cornea reflected bright spot image corresponding to reflected light on a cornea of the subject's eye, and
    wherein the positional relationship change unit changes the positional relationship based on the cornea reflected bright spot image.

4. The ophthalmologic apparatus according to claim 1, further comprising:
    a display control unit configured to display on a display unit a cornea reflected bright spot image corresponding to reflected light on a cornea of the subject's eye based on the measurement result of the aberration measurement unit, and an input unit configured to input a signal for changing the positional relationship.

5. The ophthalmologic apparatus according to claim 1, wherein the irradiation state change unit changes an irradiation position on the anterior eye of the subject's eye with the measurement light.

6. The ophthalmologic apparatus according to claim 1, wherein the irradiation state change unit includes a movement unit configured to move an optical axis of an optical system including a light source, which generates the measurement light, from an optical axis of the subject's eye.

7. The ophthalmologic apparatus according to claim 1, wherein the first irradiation state is a state where a position including a substantial center of the anterior eye of the subject's eye is irradiated with the measurement light, and the second irradiation state is a state where a position not including a substantial center of the anterior eye of the subject's eye is irradiated with the measurement light.

8. The ophthalmologic apparatus according to claim 1, wherein the irradiation state change unit changes an irradiation shape on the anterior eye of the subject's eye with the measurement light.

9. The ophthalmologic apparatus according to claim 8, wherein the irradiation state change unit changes the irradiation shape with an optical axis of an optical system including a light source, which generates the measurement light, and an optical axis of the subject's eye substantially matched.

10. The ophthalmologic apparatus according to claim 1, wherein the irradiation state change unit changes an irradiation area on the anterior eye of the subject's eye with the measurement light.

11. The ophthalmologic apparatus according to claim 10, wherein the irradiation state change unit changes the irradiation area with an optical axis of an optical system including a light source, which generates the measurement light, and an optical axis of the subject's eye not matched.

12. The ophthalmologic apparatus according to claim 1, further comprising:
a determination unit configured to determine that the change in the positional relationship has been completed,
wherein the irradiation state change unit changes the irradiation state of the anterior eye of the subject's eye with the measurement light from the first irradiation state to the second irradiation state according to a determination result of the determination unit.

13. The ophthalmologic apparatus according to claim 12, further comprising:
a designation unit configured to designate either one of a change mode for changing the positional relationship and a measurement mode for measuring the aberration of the subject's eye,
wherein the determination unit determines that the change in the positional relationship has been completed when the change mode has been designated, and
wherein the designation unit designates the measurement mode according to the determination result of the determination unit.

14. The ophthalmologic apparatus according to claim 1, wherein the aberration measurement unit is a Shack-Hartmann wavefront sensor.

15. The ophthalmologic apparatus according to claim 1, further comprising:
an aberration correction unit configured to correct the aberration included in the measurement light based on the aberration measured by the aberration measurement unit in the second irradiation state, and
an image acquisition unit configured to acquire an image of the subject's eye, which has been irradiated with the corrected measurement light, based on return light from the subject's eye.

16. A method for controlling an ophthalmologic apparatus, the method comprising:
changing a positional relationship between a subject's eye and an optical system including an aberration measurement unit in a first irradiation state of an anterior eye of the subject's eye with measurement light;
changing an irradiation state of the anterior eye of the subject's eye with the measurement light from the first irradiation state to a second irradiation state; and
correcting an aberration of the subject's eye based on a measurement result of an aberration of the subject's eye in the second irradiation state.

* * * * *